(12) United States Patent
Demmer et al.

(10) Patent No.: US 9,492,669 B2
(45) Date of Patent: Nov. 15, 2016

(54) MODE SWITCHING BY A VENTRICULAR LEADLESS PACING DEVICE

(71) Applicant: Medtronic, Inc., Minneapolis, MN (US)

(72) Inventors: Wade M Demmer, Coon Rapids, MN (US); Todd J Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 45 days.

(21) Appl. No.: 14/538,486

(22) Filed: Nov. 11, 2014

(65) Prior Publication Data

US 2016/0129263 A1 May 12, 2016

(51) Int. Cl.
*A61N 1/365* (2006.01)
*A61N 1/37* (2006.01)
*A61N 1/375* (2006.01)
*A61N 1/362* (2006.01)
*A61N 1/372* (2006.01)

(52) U.S. Cl.
CPC ............. *A61N 1/3702* (2013.01); *A61N 1/365* (2013.01); *A61N 1/3627* (2013.01); *A61N 1/3756* (2013.01); *A61N 1/37205* (2013.01); *A61N 1/36507* (2013.01)

(58) Field of Classification Search
CPC .............................. A61N 1/3756; A61N 1/365
See application file for complete search history.

(56) References Cited

U.S. PATENT DOCUMENTS

| | | |
|---|---|---|
| 3,486,506 A | 12/1969 | Auphan |
| 3,659,615 A | 5/1972 | Enger |
| 3,693,625 A | 9/1972 | Auphan |
| 3,835,864 A | 9/1974 | Rasor et al. |
| 3,943,936 A | 3/1976 | Rasor et al. |
| 4,157,720 A | 6/1979 | Greatbatch |
| RE30,366 E | 8/1980 | Rasor et al. |
| 4,256,115 A | 3/1981 | Bilitch |
| 4,333,469 A | 6/1982 | Jeffcoat et al. |
| 5,144,949 A | 9/1992 | Olson |
| 5,170,784 A | 12/1992 | Ramon et al. |

(Continued)

FOREIGN PATENT DOCUMENTS

| | | |
|---|---|---|
| CN | 101185789 A | 5/2008 |
| CN | 101284160 A | 10/2008 |

(Continued)

OTHER PUBLICATIONS

Sheldon, et al., "Mode Switching by a Ventricular Leadless Pacing Device", U.S. Appl. No. 14/538,518, filed Nov. 11, 2014, 73 pages.

(Continued)

*Primary Examiner* — George Evanisko
(74) *Attorney, Agent, or Firm* — Evans M. Mburu

(57) ABSTRACT

In some examples, a leadless pacing device (hereinafter, "LPD") is configured for implantation in a ventricle of a heart of a patient, and is configured to switch between an atrio-ventricular synchronous pacing mode and an asynchronous ventricular pacing mode in response to detection of one or more sensing events, which may be, for example, undersensing events. In some examples, an LPD is configured to switch from a sensing without pacing mode to an atrio-ventricular synchronous pacing mode in response to determining, for a threshold number of cardiac cycles, a ventricular depolarization was not detected within a ventricular event detection window that begins at an atrial activation event.

29 Claims, 13 Drawing Sheets

(56) References Cited

U.S. PATENT DOCUMENTS

| | | |
|---|---|---|
| 5,193,539 A | 3/1993 | Schulman et al. |
| 5,193,540 A | 3/1993 | Schulman et al. |
| 5,237,992 A | 8/1993 | Poore |
| 5,243,977 A | 9/1993 | Trabucco et al. |
| 5,312,439 A | 5/1994 | Loeb |
| 5,324,316 A | 6/1994 | Schulman et al. |
| 5,391,189 A | 2/1995 | van Krieken et al. |
| 5,404,877 A | 4/1995 | Nolan et al. |
| 5,405,367 A | 4/1995 | Schulman et al. |
| 5,411,535 A | 5/1995 | Fujii et al. |
| 5,441,527 A | 8/1995 | Erickson et al. |
| 5,454,836 A | 10/1995 | van der Veen et al. |
| 5,540,728 A | 7/1996 | Shelton et al. |
| 5,674,259 A | 10/1997 | Gray |
| 5,792,208 A | 8/1998 | Gray |
| 5,814,089 A | 9/1998 | Stokes et al. |
| 5,843,132 A | 12/1998 | Ilvento |
| 5,893,882 A | 4/1999 | Peterson et al. |
| 5,895,414 A | 4/1999 | Sanchez-Zambrano |
| 5,954,757 A | 9/1999 | Gray |
| 5,970,986 A | 10/1999 | Bolz et al. |
| 5,987,352 A | 11/1999 | Klein et al. |
| 6,044,300 A | 3/2000 | Gray |
| 6,051,017 A | 4/2000 | Loeb et al. |
| 6,129,745 A | 10/2000 | Sun et al. |
| 6,141,588 A | 10/2000 | Cox et al. |
| 6,144,879 A | 11/2000 | Gray et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,214,032 B1 | 4/2001 | Loeb et al. |
| 6,240,316 B1 | 5/2001 | Richmond et al. |
| 6,315,721 B2 | 11/2001 | Schulman et al. |
| 6,321,115 B1 | 11/2001 | Mouchawar et al. |
| 6,415,184 B1 | 7/2002 | Ishikawa et al. |
| 6,434,424 B1 | 8/2002 | Igel et al. |
| 6,445,953 B1 | 9/2002 | Bulkes et al. |
| 6,477,420 B1 | 11/2002 | Struble et al. |
| 6,592,518 B2 | 7/2003 | Denker et al. |
| 6,628,989 B1 | 9/2003 | Penner et al. |
| 6,654,638 B1 | 11/2003 | Sweeney |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,672 B2 | 5/2004 | Schulman et al. |
| 6,764,446 B2 | 7/2004 | Wolinsky et al. |
| 6,788,975 B1 | 9/2004 | Whitehurst et al. |
| 6,804,561 B2 | 10/2004 | Stover |
| 6,819,955 B2 | 11/2004 | Levine |
| 6,871,099 B1 | 3/2005 | Whitehurst et al. |
| 6,904,315 B2 | 6/2005 | Panken et al. |
| 6,907,285 B2 | 6/2005 | Denker et al. |
| 6,917,833 B2 | 7/2005 | Denker et al. |
| 6,941,171 B2 | 9/2005 | Mann et al. |
| 6,947,782 B2 | 9/2005 | Schulman et al. |
| 7,003,350 B2 | 2/2006 | Denker et al. |
| 7,006,864 B2 | 2/2006 | Echt et al. |
| 7,024,248 B2 | 4/2006 | Penner et al. |
| 7,050,849 B2 | 5/2006 | Echt et al. |
| 7,054,692 B1 | 5/2006 | Whitehurst et al. |
| 7,082,336 B2 | 7/2006 | Ransbury et al. |
| 7,103,408 B2 | 9/2006 | Haller et al. |
| 7,114,502 B2 | 10/2006 | Schulman et al. |
| 7,120,992 B2 | 10/2006 | He et al. |
| 7,132,173 B2 | 11/2006 | Daulton |
| 7,167,751 B1 | 1/2007 | Whitehurst et al. |
| 7,177,698 B2 | 2/2007 | Klosterman et al. |
| 7,184,830 B2 | 2/2007 | Echt et al. |
| 7,198,603 B2 | 4/2007 | Penner et al. |
| 7,200,437 B1 | 4/2007 | Nabutovsky et al. |
| 7,203,548 B2 | 4/2007 | Whitehurst et al. |
| 7,214,189 B2 | 5/2007 | Zdeblick |
| 7,236,821 B2 | 6/2007 | Cates et al. |
| 7,236,829 B1 | 6/2007 | Farazi et al. |
| 7,260,436 B2 | 8/2007 | Kilgore et al. |
| 7,283,874 B2 | 10/2007 | Penner |
| 7,286,883 B2 | 10/2007 | Schulman et al. |
| 7,292,890 B2 | 11/2007 | Whitehurst et al. |
| 7,294,108 B1 | 11/2007 | Bornzin et al. |
| 7,295,879 B2 | 11/2007 | Denker et al. |
| 7,310,556 B2 | 12/2007 | Bulkes |
| 7,330,756 B2 | 2/2008 | Marnfeldt |
| 7,343,204 B2 | 3/2008 | Schulman et al. |
| 7,351,921 B1 | 4/2008 | Haller et al. |
| 7,363,082 B2 | 4/2008 | Ransbury et al. |
| 7,376,461 B2 | 5/2008 | Perschbacher et al. |
| 7,428,438 B2 | 9/2008 | Parramon et al. |
| 7,437,193 B2 | 10/2008 | Parramon et al. |
| 7,444,180 B2 | 10/2008 | Kuzma et al. |
| 7,450,998 B2 | 11/2008 | Zilberman et al. |
| 7,493,172 B2 | 2/2009 | Whitehurst et al. |
| 7,513,257 B2 | 4/2009 | Schulman et al. |
| 7,519,421 B2 | 4/2009 | Denker et al. |
| 7,519,424 B2 | 4/2009 | Dennis et al. |
| 7,529,589 B2 | 5/2009 | Williams et al. |
| 7,532,932 B2 | 5/2009 | Denker et al. |
| 7,532,933 B2 | 5/2009 | Hastings et al. |
| 7,535,296 B2 | 5/2009 | Bulkes et al. |
| 7,555,345 B2 | 6/2009 | Wahlstrand et al. |
| 7,558,631 B2 | 7/2009 | Cowan et al. |
| 7,565,195 B1 | 7/2009 | Kroll et al. |
| 7,587,241 B2 | 9/2009 | Parramon et al. |
| 7,606,621 B2 | 10/2009 | Brisken et al. |
| 7,610,092 B2 | 10/2009 | Cowan et al. |
| 7,616,990 B2 | 11/2009 | Chavan et al. |
| 7,616,992 B2 | 11/2009 | Dennis et al. |
| 7,617,007 B2 | 11/2009 | Williams et al. |
| 7,627,371 B2 | 12/2009 | Wang et al. |
| 7,627,376 B2 | 12/2009 | Dennis et al. |
| 7,627,383 B2 | 12/2009 | Haller et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,640,061 B2 | 12/2009 | He et al. |
| 7,647,109 B2 | 1/2010 | Hastings et al. |
| 7,650,186 B2 | 1/2010 | Hastings et al. |
| 7,706,892 B2 | 4/2010 | Colvin et al. |
| 7,713,194 B2 | 5/2010 | Zdeblick |
| 7,734,343 B2 | 6/2010 | Ransbury et al. |
| 7,747,335 B2 | 6/2010 | Williams |
| 7,751,881 B2 | 7/2010 | Cowan et al. |
| 7,766,216 B2 | 8/2010 | Daulton |
| 7,771,838 B1 | 8/2010 | He et al. |
| 7,781,683 B2 | 8/2010 | Haller et al. |
| 7,809,438 B2 | 10/2010 | Echt et al. |
| 7,822,480 B2 | 10/2010 | Park et al. |
| 7,826,903 B2 | 11/2010 | Denker et al. |
| 7,840,282 B2 | 11/2010 | Williams et al. |
| 7,848,815 B2 | 12/2010 | Brisken et al. |
| 7,848,823 B2 | 12/2010 | Drasler et al. |
| 7,860,564 B2 | 12/2010 | Root et al. |
| 7,860,570 B2 | 12/2010 | Whitehurst et al. |
| 7,890,173 B2 | 2/2011 | Brisken et al. |
| 7,894,907 B2 | 2/2011 | Cowan et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,904,167 B2 | 3/2011 | Klosterman et al. |
| 7,930,031 B2 | 4/2011 | Penner |
| 7,937,148 B2 | 5/2011 | Jacobson |
| 7,945,333 B2 | 5/2011 | Jacobson |
| 7,957,805 B2 | 6/2011 | He |
| 7,979,126 B2 | 7/2011 | Payne et al. |
| 7,991,467 B2 | 8/2011 | Markowitz et al. |
| 7,996,097 B2 | 8/2011 | DiBernardo et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,032,227 B2 | 10/2011 | Parramon et al. |
| 8,078,279 B2 | 12/2011 | Dennis et al. |
| 8,078,283 B2 | 12/2011 | Cowan et al. |

(56) References Cited

U.S. PATENT DOCUMENTS

| | | |
|---|---|---|
| 8,116,883 B2 | 2/2012 | Williams et al. |
| 8,126,561 B2 | 2/2012 | Chavan et al. |
| 8,127,424 B2 | 3/2012 | Haller et al. |
| 8,165,696 B2 | 4/2012 | McClure et al. |
| 8,185,212 B2 | 5/2012 | Carbunaru et al. |
| 8,204,595 B2 | 6/2012 | Pianca et al. |
| 8,224,449 B2 | 7/2012 | Carbunaru et al. |
| 8,239,045 B2 | 8/2012 | Ransbury et al. |
| 8,240,780 B1 | 8/2012 | Klimes |
| 8,295,939 B2 | 10/2012 | Jacobson |
| 8,301,242 B2 | 10/2012 | Root et al. |
| 8,301,262 B2 | 10/2012 | Mi et al. |
| 8,311,627 B2 | 11/2012 | Root et al. |
| 8,315,701 B2 | 11/2012 | Cowan et al. |
| 8,321,036 B2 | 11/2012 | Brockway et al. |
| 8,332,036 B2 | 12/2012 | Hastings et al. |
| 8,340,780 B2 | 12/2012 | Hastings et al. |
| 8,352,025 B2 | 1/2013 | Jacobson |
| 8,352,028 B2 | 1/2013 | Wenger |
| 8,359,098 B2 | 1/2013 | Lund et al. |
| 8,364,267 B2 | 1/2013 | Schleicher et al. |
| 8,364,276 B2 | 1/2013 | Willis |
| 8,364,278 B2 | 1/2013 | Pianca et al. |
| 8,364,280 B2 | 1/2013 | Marnfeldt et al. |
| 8,368,051 B2 | 2/2013 | Ting et al. |
| 8,374,696 B2 | 2/2013 | Sanchez et al. |
| 8,386,051 B2 | 2/2013 | Rys |
| 8,457,742 B2 | 6/2013 | Jacobson |
| 8,478,408 B2 | 7/2013 | Hastings et al. |
| 8,478,431 B2 | 7/2013 | Griswold et al. |
| 8,489,205 B2 | 7/2013 | Stotts et al. |
| 8,494,637 B2 | 7/2013 | Cowan et al. |
| 8,494,642 B2 | 7/2013 | Cowan et al. |
| 8,494,644 B2 | 7/2013 | Cowan et al. |
| 8,504,156 B2 | 8/2013 | Bonner et al. |
| 8,527,068 B2 | 9/2013 | Ostroff |
| 8,532,790 B2 | 9/2013 | Griswold |
| 8,541,131 B2 | 9/2013 | Lund et al. |
| 8,543,190 B2 | 9/2013 | Wasson et al. |
| 8,543,204 B2 | 9/2013 | Demmer et al. |
| 8,543,205 B2 | 9/2013 | Ostroff |
| 8,543,216 B2 | 9/2013 | Carbunaru et al. |
| 8,548,605 B2 | 10/2013 | Ollivier |
| 8,560,892 B2 | 10/2013 | Nicholes |
| 8,565,897 B2 | 10/2013 | Regnier et al. |
| 8,588,926 B2 | 11/2013 | Moore et al. |
| 8,626,294 B2 | 1/2014 | Sheldon et al. |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,639,336 B2 | 1/2014 | Bornzin et al. |
| 8,644,922 B2 | 2/2014 | Root et al. |
| 8,660,660 B2 | 2/2014 | Dai et al. |
| 8,670,842 B1 | 3/2014 | Bornzin et al. |
| 8,750,976 B2 | 6/2014 | Stadler et al. |
| 2002/0183794 A1 | 12/2002 | Struble |
| 2003/0078627 A1 | 4/2003 | Casavant et al. |
| 2003/0114905 A1 | 6/2003 | Kuzma |
| 2003/0125777 A1 * | 7/2003 | Ding .................. A61N 1/3712 607/27 |
| 2003/0204208 A1 | 10/2003 | Kramm |
| 2004/0015204 A1 | 1/2004 | Whitehurst et al. |
| 2004/0073267 A1 | 4/2004 | Holzer |
| 2004/0093039 A1 | 5/2004 | Schumert |
| 2004/0122477 A1 | 6/2004 | Whitehurst et al. |
| 2004/0133242 A1 | 7/2004 | Chapman et al. |
| 2004/0143299 A1 | 7/2004 | Casavant et al. |
| 2004/0147973 A1 | 7/2004 | Hauser |
| 2004/0162590 A1 | 8/2004 | Whitehurst et al. |
| 2004/0172089 A1 | 9/2004 | Whitehurst et al. |
| 2005/0055061 A1 | 3/2005 | Holzer |
| 2005/0070962 A1 | 3/2005 | Echt et al. |
| 2005/0256549 A1 | 11/2005 | Holzer |
| 2005/0288717 A1 | 12/2005 | Sunagawa |
| 2006/0074449 A1 | 4/2006 | Denker et al. |
| 2006/0135999 A1 | 6/2006 | Bodner et al. |
| 2006/0136005 A1 | 6/2006 | Brisken et al. |
| 2006/0173497 A1 | 8/2006 | Mech et al. |
| 2006/0241705 A1 | 10/2006 | Neumann et al. |
| 2006/0241732 A1 | 10/2006 | Denker et al. |
| 2007/0027508 A1 | 2/2007 | Cowan et al. |
| 2007/0060961 A1 | 3/2007 | Echt et al. |
| 2007/0073353 A1 | 3/2007 | Rooney et al. |
| 2007/0075905 A1 | 4/2007 | Denker et al. |
| 2007/0078490 A1 | 4/2007 | Cowan et al. |
| 2007/0088396 A1 | 4/2007 | Jacobson |
| 2007/0088397 A1 | 4/2007 | Jacobson |
| 2007/0106332 A1 | 5/2007 | Denker et al. |
| 2007/0106357 A1 | 5/2007 | Denker et al. |
| 2007/0118187 A1 | 5/2007 | Denker et al. |
| 2007/0129773 A1 | 6/2007 | Bulkes |
| 2007/0135850 A1 | 6/2007 | Amblard |
| 2007/0135883 A1 | 6/2007 | Drasler et al. |
| 2007/0150037 A1 | 6/2007 | Hastings et al. |
| 2007/0156204 A1 | 7/2007 | Denker et al. |
| 2007/0185538 A1 | 8/2007 | Denker et al. |
| 2007/0210862 A1 | 9/2007 | Denker et al. |
| 2007/0219590 A1 | 9/2007 | Hastings et al. |
| 2007/0276444 A1 | 11/2007 | Gelbart et al. |
| 2007/0288076 A1 | 12/2007 | Bulkes et al. |
| 2007/0288077 A1 | 12/2007 | Bulkes et al. |
| 2007/0293904 A1 | 12/2007 | Gelbart et al. |
| 2007/0293908 A1 | 12/2007 | Cowan et al. |
| 2007/0293912 A1 | 12/2007 | Cowan et al. |
| 2007/0293913 A1 | 12/2007 | Cowan et al. |
| 2008/0033497 A1 | 2/2008 | Bulkes et al. |
| 2008/0039904 A1 | 2/2008 | Bulkes et al. |
| 2008/0051854 A1 | 2/2008 | Bulkes et al. |
| 2008/0058886 A1 | 3/2008 | Williams |
| 2008/0077184 A1 | 3/2008 | Denker et al. |
| 2008/0077188 A1 | 3/2008 | Denker et al. |
| 2008/0097529 A1 | 4/2008 | Parramon et al. |
| 2008/0109054 A1 | 5/2008 | Hastings et al. |
| 2008/0119911 A1 | 5/2008 | Rosero |
| 2008/0132961 A1 | 6/2008 | Jaax et al. |
| 2008/0140154 A1 | 6/2008 | Loeb et al. |
| 2008/0255628 A1 | 10/2008 | Seim |
| 2008/0288039 A1 | 11/2008 | Reddy |
| 2008/0294208 A1 | 11/2008 | Willis et al. |
| 2008/0294210 A1 | 11/2008 | Rosero |
| 2008/0319502 A1 | 12/2008 | Sunagawa et al. |
| 2009/0024180 A1 | 1/2009 | Kisker et al. |
| 2009/0048583 A1 | 2/2009 | Williams et al. |
| 2009/0082827 A1 | 3/2009 | Kveen et al. |
| 2009/0082828 A1 | 3/2009 | Ostroff |
| 2009/0171408 A1 | 7/2009 | Solem |
| 2009/0192570 A1 | 7/2009 | Jaax et al. |
| 2009/0198293 A1 | 8/2009 | Cauller et al. |
| 2009/0198295 A1 | 8/2009 | Dennis et al. |
| 2009/0198308 A1 | 8/2009 | Gross et al. |
| 2009/0281587 A1 | 11/2009 | Pei |
| 2009/0299426 A1 | 12/2009 | Kim et al. |
| 2009/0326601 A1 | 12/2009 | Brisken et al. |
| 2010/0094367 A1 | 4/2010 | Sen |
| 2010/0161002 A1 | 6/2010 | Aghassian et al. |
| 2010/0179628 A1 | 7/2010 | Towe et al. |
| 2010/0249883 A1 | 9/2010 | Zdeblick |
| 2010/0249885 A1 | 9/2010 | Colvin et al. |
| 2010/0286744 A1 | 11/2010 | Echt et al. |
| 2010/0304209 A1 | 12/2010 | Lund et al. |
| 2010/0305627 A1 | 12/2010 | Anderson |
| 2010/0305628 A1 | 12/2010 | Lund et al. |
| 2010/0305629 A1 | 12/2010 | Lund et al. |
| 2010/0312320 A1 | 12/2010 | Faltys et al. |
| 2011/0054555 A1 | 3/2011 | Williams et al. |
| 2011/0060392 A1 | 3/2011 | Zdeblick et al. |
| 2011/0071585 A1 | 3/2011 | Ransbury et al. |
| 2011/0071586 A1 | 3/2011 | Jacobson |
| 2011/0077708 A1 | 3/2011 | Ostroff |
| 2011/0077721 A1 | 3/2011 | Whitehurst et al. |
| 2011/0137378 A1 | 6/2011 | Klosterman et al. |
| 2011/0160801 A1 | 6/2011 | Markowitz et al. |
| 2011/0208260 A1 | 8/2011 | Jacobson |
| 2011/0245782 A1 | 10/2011 | Berthiaume et al. |

(56) References Cited

U.S. PATENT DOCUMENTS

| | | |
|---|---|---|
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0301656 A1 | 12/2011 | Casavant et al. |
| 2011/0313490 A1 | 12/2011 | Parramon et al. |
| 2012/0059431 A1 | 3/2012 | Williams et al. |
| 2012/0081201 A1 | 4/2012 | Norgaard et al. |
| 2012/0095521 A1 | 4/2012 | Hintz |
| 2012/0095539 A1 | 4/2012 | Khairkhahan et al. |
| 2012/0109149 A1 | 5/2012 | Bonner et al. |
| 2012/0109236 A1 | 5/2012 | Jacobson et al. |
| 2012/0116489 A1 | 5/2012 | Khairkhahan et al. |
| 2012/0143271 A1 | 6/2012 | Root et al. |
| 2012/0158090 A1 | 6/2012 | Chavan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0179219 A1 | 7/2012 | Kisker et al. |
| 2012/0197352 A1 | 8/2012 | Carbunaru et al. |
| 2012/0197373 A1 | 8/2012 | Khairkhahan et al. |
| 2012/0232371 A1 | 9/2012 | Mech et al. |
| 2012/0290021 A1 | 11/2012 | Saurkar et al. |
| 2012/0290025 A1 | 11/2012 | Keimel |
| 2012/0316622 A1 | 12/2012 | Whitehurst et al. |
| 2012/0323099 A1 | 12/2012 | Mothilal et al. |
| 2013/0023975 A1 | 1/2013 | Locsin |
| 2013/0030483 A1 | 1/2013 | Demmer et al. |
| 2013/0035748 A1 | 2/2013 | Bonner et al. |
| 2013/0066169 A1 | 3/2013 | Rys et al. |
| 2013/0073004 A1 | 3/2013 | Root et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103109 A1 | 4/2013 | Jacobson |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0123872 A1 | 5/2013 | Bornzin et al. |
| 2013/0123875 A1 | 5/2013 | Varady et al. |
| 2013/0131159 A1 | 5/2013 | Ko et al. |
| 2013/0131693 A1 | 5/2013 | Berthiaume et al. |
| 2013/0138004 A1 | 5/2013 | Dong et al. |
| 2013/0138006 A1 | 5/2013 | Bornzin et al. |
| 2013/0150695 A1 | 6/2013 | Biela et al. |
| 2013/0184790 A1 | 7/2013 | Schleicher et al. |
| 2013/0226259 A1 | 8/2013 | Penner et al. |
| 2013/0231710 A1 | 9/2013 | Jacobson |
| 2013/0234692 A1 | 9/2013 | Liang et al. |
| 2013/0235663 A1 | 9/2013 | Walsh et al. |
| 2013/0235672 A1 | 9/2013 | Walsh et al. |
| 2013/0238044 A1 | 9/2013 | Penner |
| 2013/0238056 A1 | 9/2013 | Poore et al. |
| 2013/0238072 A1 | 9/2013 | Deterre et al. |
| 2013/0238073 A1 | 9/2013 | Makdissi et al. |
| 2013/0238840 A1 | 9/2013 | Walsh et al. |
| 2013/0253309 A1 | 9/2013 | Allan et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijis et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0289428 A1 | 10/2013 | Patel et al. |
| 2013/0302665 A1 | 11/2013 | Zhao et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012342 A1 | 1/2014 | Penner et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0026016 A1 | 1/2014 | Nicholes |
| 2014/0031836 A1 | 1/2014 | Ollivier |
| 2014/0031837 A1 | 1/2014 | Perryman et al. |
| 2014/0039570 A1 | 2/2014 | Carroll et al. |
| 2014/0039578 A1 | 2/2014 | Whitehurst et al. |
| 2014/0039588 A1 | 2/2014 | Ok et al. |
| 2014/0039591 A1 | 2/2014 | Drasler et al. |
| 2014/0046395 A1 | 2/2014 | Regnier et al. |
| 2014/0058240 A1 | 2/2014 | Mothilal et al. |
| 2014/0072872 A1 | 3/2014 | Hodgkinson et al. |
| 2014/0100627 A1 | 4/2014 | Min |
| 2014/0121720 A1 | 5/2014 | Bonner et al. |

FOREIGN PATENT DOCUMENTS

| | | |
|---|---|---|
| EP | 0709114 A2 | 5/1996 |
| EP | 1541191 A1 | 6/2005 |
| EP | 1 731 195 A1 | 12/2006 |
| EP | 1549393 B1 | 2/2008 |
| TW | 1251986 B | 3/2006 |
| TW | 1252007 B | 3/2006 |
| WO | 2006099425 A1 | 9/2006 |
| WO | 2009006531 A1 | 1/2009 |
| WO | 2009052480 A2 | 4/2009 |
| WO | 2012154599 A2 | 11/2012 |
| WO | 2013080038 A2 | 6/2013 |
| WO | 2012150000 | 11/2013 |
| WO | 2014046662 | 3/2014 |
| WO | 2014/178035 A1 | 11/2014 |

OTHER PUBLICATIONS

Demmer, et al., "Ventricular Leadless Pacing Device Mode Switching", U.S. Appl. No. 14/694,976, filed Apr. 23, 2015, 97 pages.
US 8,116,861, 2/2011, Root et al. (withdrawn).
(PCT/US2015/058743) PCT Notification of Transmittal of the International Search Report and the Written Opinion of the International Searching Authority, mailed Mar. 8, 2016, 11 pages.
(PCT/US2015/058739) PCT Notification of Transmittal of the International Search Report and the Written Opinion of the International Searching Authority, mailed Jan. 20, 2016, 11 pages.
(PCT/US2015/058745) PCT Notification of Transmittal of the International Search Report and the Written Opinion of the International Searching Authority, mailed Feb. 3, 2016, 11 pages.

* cited by examiner

MODE SWITCHING BY A VENTRICULAR LEADLESS PACING DEVICE

TECHNICAL FIELD

The disclosure relates to cardiac pacing, and more particularly, to cardiac pacing using a leadless pacing device.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at a target site. The pulse generator may provide electrical stimulation to the target site and/or monitor cardiac electrical activity at the target site via the electrodes.

A leadless pacing device has also been proposed for sensing electrical activity and/or delivering therapeutic electrical signals to the heart. The leadless pacing device may include one or more electrodes on its outer housing to deliver therapeutic electrical signals and/or sense intrinsic depolarizations of the heart. The leadless pacing device may be positioned within or outside of the heart and, in some examples, may be anchored to a wall of the heart via a fixation mechanism.

SUMMARY

The disclosure describes a leadless pacing device (hereinafter, "LPD") that is configured for implantation in a ventricle of a heart of a patient, and is configured to switch from a sensing without pacing mode to an atrio-ventricular synchronous pacing mode in response to detection of one or more ventricular undersensing events. In some examples, the LPD is also configured to switch between an atrio-ventricular synchronous pacing mode and an asynchronous ventricular pacing mode in response to detection of one or more atrial undersensing events. In an atrio-ventricular synchronous pacing mode, the LPD times the delivery of a pacing pulse to a ventricle of a heart of a patient relative to an atrial activation event, which may be an event that leads to a contraction of an atrium. In the asynchronous ventricular pacing mode, the LPD is configured to deliver a ventricular pacing pulse if it does not detect an intrinsic ventricular depolarization within a VV interval that begins when a previous intrinsic ventricular depolarization was detected, or when a previous ventricular pacing pulse was delivered.

In some examples, while the LPD is in an atrio-ventricular synchronous pacing mode, a processing module of a therapy system including the LPD may determine, e.g., based on an electrical cardiac signal, whether an atrial activation event of the heart is detected within an atrial activation event detection window that begins at a ventricular activation event. In response to determining the atrial activation event is detected within the atrial activation event detection window and in response to further determining a ventricular activation event was not detected subsequent to the detected atrial activation event (e.g., within an atrioventricular (AV) interval beginning when the atrial activation event was detected), the processing module may control the LPD to deliver a ventricular pacing pulse according to the atrio-ventricular synchronous pacing mode. However, if the processing module does not detect an atrial activation event within the atrial activation event detection window, and determines that an atrial activation event was not detected within atrial activation event detection windows for a threshold number of cardiac cycles, then the processing module may detect an undersensing event. In response to detecting the undersensing event, the processing module may control the LPD to switch from the atrio-ventricular synchronous pacing mode to an asynchronous ventricular pacing mode.

In one aspect, the disclosure is directed to a method comprising receiving, by a processing module, an electrical cardiac signal of a patient sensed by a leadless pacing device while the leadless pacing device is in a sensing without pacing mode; detecting, by the processing module and based on the electrical cardiac signal, an atrial activation event; determining, by the processing module and based on the electrical cardiac signal, a ventricular sense event was not detected within a ventricular event detection window that begins at the atrial activation event; and controlling, by the processing module, the leadless pacing device to switch from the sensing without pacing mode to an atrio-ventricular synchronous pacing mode based on the determination that the ventricular sense event was not detected within the ventricular event detection window, wherein controlling the leadless pacing device to switch to the atrio-ventricular synchronous pacing mode comprises controlling the leadless pacing device to deliver a pacing pulse to the patient according to the atrio-ventricular synchronous pacing mode.

In another aspect, the disclosure is directed to a leadless pacing system comprising a leadless pacing device configured to sense an electric cardiac signal and configured to operate in a sensing without pacing mode and an atrio-ventricular pacing mode, and a processing module configured to receive the electrical cardiac signal sensed by a leadless pacing device while the leadless pacing device is in the sensing without pacing mode, detect, based on the electrical cardiac signal, an atrial activation event, determine, based on the electrical cardiac signal, a ventricular sense event was not detected within a ventricular event detection window that begins at the atrial activation event, and control the leadless pacing device to switch from the sensing without pacing mode to an atrio-ventricular synchronous pacing mode based on the determination that the ventricular sense event was not detected within the ventricular event detection window, wherein the processing module is configured to control the leadless pacing device to switch to the atrio-ventricular synchronous pacing mode by at least controlling the leadless pacing device to deliver a pacing pulse to the patient according to the atrio-ventricular synchronous pacing mode.

In another aspect, the disclosure is directed to a system comprising means for detecting, based on the electrical cardiac signal sensed by a leadless pacing device while the leadless pacing device is in a sensing without pacing mode, an atrial activation event; means for determining, based on the electrical cardiac signal, a ventricular sense event was not detected within a ventricular event detection window that begins at the atrial activation event; and means for controlling the leadless pacing device to switch from the sensing without pacing mode to an atrio-ventricular synchronous pacing mode based on the determination that the ventricular sense event was not detected within the ventricular event detection window by at least controlling the leadless pacing device to deliver a pacing pulse to the patient according to the atrio-ventricular synchronous pacing mode.

In another aspect, the disclosure is directed to a computer-readable storage medium comprising instructions that, when executed by a processing module, cause the processing module to: detect, based on an electrical cardiac signal sensed by a leadless pacing device while the leadless pacing device is in a sensing without pacing mode, an atrial activation event, an atrial activation event; determine, based on the electrical cardiac signal, a ventricular sense event was not detected within a ventricular event detection window that begins at the atrial activation event; and control the leadless pacing device to switch from the sensing without pacing mode to an atrio-ventricular synchronous pacing mode based on the determination that the ventricular sense event was not detected within the ventricular event detection window, wherein controlling the leadless pacing device to switch to the atrio-ventricular synchronous pacing mode comprises controlling the leadless pacing device to deliver a pacing pulse to the patient according to the atrio-ventricular synchronous pacing mode.

In another aspect, the disclosure is directed to a method comprising receiving, by a processing module, an electrical cardiac signal sensed by a leadless pacing device while the leadless pacing device is in an atrio-ventricular synchronous pacing mode; detecting, by a processing module, a first atrial activation event; determining, by a processing module and based on the electrical cardiac signal, a second atrial activation event was not detected within a detection window that begins at the first atrial activation event; and controlling, by the processing module, the leadless pacing device to deliver pacing pulses to a ventricle of a patient according to an asynchronous ventricular pacing mode based on the determination that the second atrial activation event was not detected within the detection window.

In another aspect, the disclosure is directed to a leadless pacing system comprising
a leadless pacing device configured to sense an electric cardiac signal and configured to deliver pacing therapy to a heart of a patient; and a processing module configured to detect, based on the electric cardiac signal and while the leadless pacing device is in an atrio-ventricular synchronous pacing mode, a first atrial activation event, determine, based on the electric cardiac signal, a second atrial activation event was not detected within a detection window that begins at the first atrial activation event, and control the leadless pacing device to deliver pacing pulses to a ventricle of a patient according to an asynchronous ventricular pacing mode based on the determination that the second atrial activation event was not detected within the detection window.

In another aspect, the disclosure is directed to a system comprising means for detecting a first atrial activation event based on an electrical cardiac signal sensed by a leadless pacing device while the leadless pacing device is in an atrio-ventricular synchronous pacing mode; means for determining, based on the electrical cardiac signal, a second atrial activation event was not detected within a detection window that begins at the first atrial activation event; and means for controlling the leadless pacing device to deliver pacing pulses to a ventricle of a patient according to an asynchronous ventricular pacing mode based on the determination that the second atrial activation event was not detected within the detection window.

In another aspect, the disclosure is directed to a computer-readable storage medium comprising instructions that, when executed by a processing module, cause the processing module to: detect, based on an electrical cardiac signal sensed by a leadless pacing device while the leadless pacing device is in an atrio-ventricular synchronous pacing mode, a first atrial activation event; determine, based on the electrical cardiac signal, a second atrial activation event was not detected within a detection window that begins at the first atrial activation event; and control the leadless pacing device to deliver pacing pulses to a ventricle of a patient according to an asynchronous ventricular pacing mode based on the determination that the second atrial activation event was not detected within the detection window.

In another aspect, the disclosure is directed to a computer-readable storage medium comprising computer-readable instructions for execution by a processor. The instructions cause a programmable processor to perform any whole or part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium is an article of manufacture and is non-transitory.

The details of one or more examples are set forth in the accompanying drawings and the description below. Other features, objects, and advantages will be apparent from the description and drawings, and from the claims.

DETAILED DESCRIPTION

Figure 1:
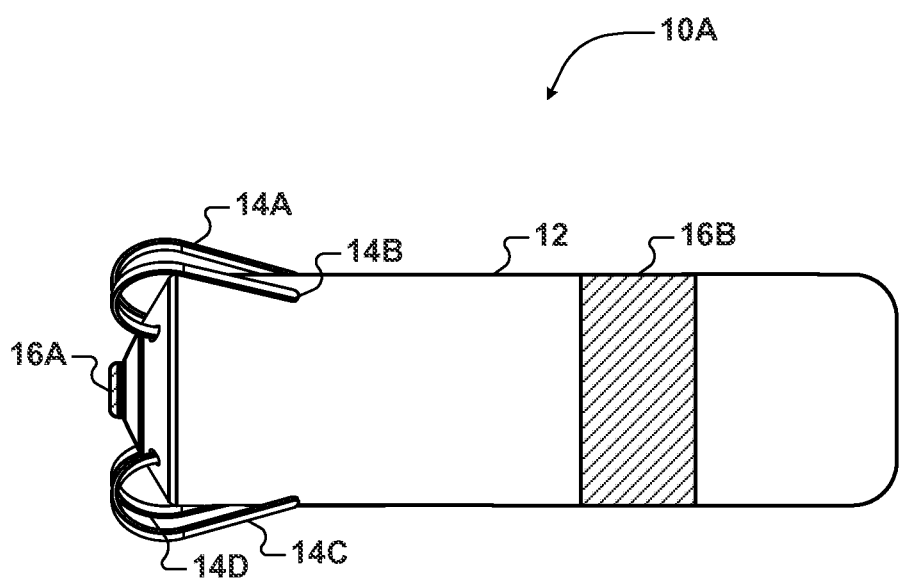
FIG. 1 is a conceptual diagram illustrating an example leadless pacing device configured to deliver atrio-ventricular synchronous pacing and asynchronous ventricular pacing.

In some cases, a dual-chamber implantable pacemaker is implanted within a pocket within a patient's chest, and coupled to a right-atrial lead and a right-ventricular lead. The right-atrial lead extends from the implantable pacemaker in the pocket to the right atrium of the patient's heart, and positions one or more electrodes within the right atrium. The right-ventricular lead extends from the implantable pacemaker in the pocket to the right ventricle of the patient's heart, and positions one or more electrodes within the right ventricle.

Such dual-chamber implantable pacemakers sense respective cardiac electrical activity, e.g., respective cardiac electrograms, via the one or more electrodes implanted within the right atrium and the one or more electrodes implanted within the right ventricle. In particular, such dual-chamber implantable pacemakers detect intrinsic atrial depolarizations via the one or more electrodes implanted within the right atrium, and intrinsic ventricular depolarizations via the one or more electrodes implanted within the right ventricle. The implantable pacemakers may also deliver pacing pulses to the right atrium and the right ventricle via the one or more electrodes in the right atrium and the right ventricle, respectively.

Due to the ability to sense both atrial and ventricular electrical activity, such dual-chamber implantable pacemakers may be able to provide atrio-ventricular synchronous pacing. For patients with intermittent AV node conduction, it may be preferable to inhibit ventricular pacing and allow an intrinsic ventricular depolarization to occur for a time, referred to as the AV interval, after an intrinsic atrial depolarization or atrial pace. Such atrio-ventricular synchronous pacing by dual-chamber implantable pacemakers is referred to as the VDD programming mode, and may be used for patients with various degrees of AV block.

Alternatively, dual-chamber implantable pacemakers may provide asynchronous ventricular pacing. Asynchronous ventricular pacing may be preferable if the patient's heart rate becomes irregular. According to an asynchronous ventricular pacing mode, the dual-chamber implantable pacemaker delivers a ventricular pacing pulse if an intrinsic ventricular depolarization is not detected within a "VV interval" that begins when a previous intrinsic depolarization was detected, or a previous ventricular pacing pulse was delivered. Such asynchronous ventricular pacing by dual-chamber implantable pacemakers is referred to as the VVI programming mode, or VVIR programming mode if the VV interval is rate-adaptive (i.e., the implantable pacemaker can sense changes in the patient's heart rate and alter the VV interval accordingly).

Implantable cardiac leads and the pocket in which pacemakers are implanted may be associated with complications. To avoid such complications, leadless pacing devices sized to be implanted entirely within the heart, e.g., in one chamber, such as the right ventricle, of the heart have been proposed. Some proposed leadless pacing devices include a plurality of electrodes that are affixed to, or are a portion of, the housing of the respective leadless pacing device ("LPD").

In some examples, a LPD described herein is configured to pace in an atrio-synchronous ventricular mode and an asynchronous ventricular mode. As discussed below, the processing module may select the mode with which the LPD delivers pacing pulses to a heart of a patient based on a detection of an atrial undersensing event.

Due to the placement of the LPD within a ventricle, the electrical activity of the right atrium sensed by the electrodes of the LPD implanted in the ventricle may be relatively low power (e.g., a low amplitude P-wave), which may cause LPD to not sense an atrial activation event based on the electrical cardiac signal. This may result in an atrial undersensing event.

In some examples, the processing module controls the LPD to switch from the atrio-synchronous ventricular pacing mode to the asynchronous ventricular pacing mode in response to detecting an atrial undersensing event. When switched from the atrio-ventricular synchronous pacing mode to the asynchronous ventricular pacing mode, the LPD terminates delivery of pacing pulses according to the atrio-ventricular synchronous and delivers pacing pulses to the patient in accordance with the asynchronous ventricular pacing mode The processing module may attempt to detect an atrial activation event (e.g., an event that leads to a contraction of an atrium) within an atrial activation event detection window begins at a ventricular activation event (e.g., an intrinsic ventricular depolarization or a delivery of a pacing pulse to the ventricle). In some examples, an atrial activation event is detection of a far field P-wave in an electrical cardiac signal sensed by the LPD implanted in the ventricle, a detection of the delivery of an atrial pacing pulse by another device (e.g., another LPD implanted in the atrium), or detection of mechanical contraction of the atrium.

In response to determining the atrial activation event was detected within the atrial activation event detection window, the processing module may control the LPD to deliver a ventricular pacing pulse according to the timing of the atrio-ventricular synchronous pacing mode. For example, in response to further determining a ventricular activation event was not detected subsequent to the detected atrial activation event (e.g., within an AV interval), the processing module may control the LPD to deliver a ventricular pacing pulse a predetermined interval of time after the detected atrial activation event.

However, in response to determining that an atrial activation event was not detected within the atrial activation event detection window, the processing module may increment an undersensing event counter or generate an undersensing indication, which may be a flag, value, or other parameter stored by a memory of the LPD or another device. The processing module may, in some examples, deliver a ventricular pacing pulse a time period (e.g., a VV interval plus offset, where the VV interval may be based on historic VV interval data or a preprogrammed VV interval) after the prior ventricular activation event.

In response to determining the counter value is greater than or equal to an undersensing event threshold value or after the processing module generates a certain number of undersensing indications (e.g., within a particular time interval), the processing module may control the LPD to switch from the atrio-ventricular synchronous pacing mode to an asynchronous ventricular pacing mode. The processing module may determine that an undersensing event occurred in response to determining the counter value is greater than or equal to a predetermined undersensing event threshold value or in response to determining number of undersensing indications is greater than or equal to a predetermined undersensing event threshold value. The predetermined undersensing event threshold value may be, for example, one, while in other examples, the predetermined threshold value may be more than one, such as two, three, or four or more.

In some examples, the counter may count the number of consecutive cardiac cycles in which an undersensing indication was generated. In other examples, the counter may count the number of cardiac cycles ("X") out of a predetermined number of consecutive cardiac cycles ("Y") in which an undersensing indication was generated. This may be referred to as an "X of Y" style counter. In other examples, the counter may count the number of cardiac cycles, within a predetermined period of time, in which an undersensing indication was generated.

In examples in which the predetermined threshold value is more than one, the LPD may not switch to the asynchronous ventricular pacing mode immediately after detection one instance of atrial undersensing. This may permit the heart of the patient to resume intrinsic conduction. In this way, the LPD may be configured to determine whether the heart resumes intrinsic conduction before switching to the asynchronous ventricular pacing mode. In some situations, the atrio-ventricular synchronous pacing mode may promote better synchrony of the heart of the patient. In at least some of these situations, the LPD may be configured to help promote better synchrony of the heart.

In some examples, an LPD is configured to operate in a sensing without pacing mode (e.g., a mode corresponding to the ODO mode of a dual chamber pacemaker with leads). For example, the LPD may operate in the sensing without pacing mode as an initial mode upon implantation of the LPD in a ventricle, prior to delivering any pacing therapy to the patient. In the sensing without pacing mode, the LPD senses electrical cardiac activity, but does not deliver any pacing therapy to the heart of the patient.

In some examples described herein, an LPD is configured to switch from a sensing without pacing mode to an atrio-ventricular synchronous pacing mode in response to detecting, while the LPD is in the sensing without pacing mode, ventricular undersensing. When the LPD switches to the atrio-ventricular synchronous pacing mode, the LPD begins delivering pacing stimulation to the patient.

Ventricular undersensing may occur when the LPD does not detect (e.g., sense), for a predetermined number of cardiac cycles, a ventricular sense event within a ventricular event detection window $V_{ACT}$ that begins at an atrial activation event (which may be an intrinsic event or the delivery of an atrial pacing pulse). A ventricular sense event may also be referred to as a ventricular depolarization event. Each occurrence of a ventricular undersensing event may indicate that the ventricle did not intrinsically conduct at the expected time following the atrial activation event. The ventricle may not intrinsically conduct due to, for example, atrioventricular (AV) block. Thus, the ventricular undersensing may occur due to AV block.

In examples in which the predetermined threshold number of ventricular events is more than one, the ventricle of the heart of the patient may not properly depolarize or contract in the cardiac cycle in which the ventricular event occurred. As a result, the heart of the patient may skip a beat. This may be referred to as a "dropping" of a heart beat by the LPD. By being configured to drop one or more heart beats, the LPD may be configured to favor the intrinsic conduction of the heart by providing time for the heart to resume intrinsic conduction or for LPD to sense the intrinsic conduction before the LPD switches to an atrio-ventricular synchronous pacing mode, in which the LPD delivers a ventricular pacing pulse that may override the intrinsic conduction of the heart. In this way, the LPD may sense the intrinsic activity of the heart for at least one full beat before delivering a ventricular pacing pulse in an atrio-ventricular synchronous pacing mode.

The predetermined threshold number of ventricular events affects the number of beats that may be dropped before the LPD switches to an atrio-ventricular synchronous pacing mode. For example, if the predetermined threshold number of ventricular events is one, then the heart may drop one beat before the LPD switches to the atrio-ventricular synchronous pacing mode. As another example, if the undersensing threshold value is two, then the heart may drop two beats before the switches to the atrio-ventricular synchronous pacing mode.

FIG. 1 is a conceptual diagram illustrating an example leadless pacing device (LPD) 10A that is configured to operating in a sensing without pacing mode, and deliver atrio-ventricular synchronous pacing and asynchronous ventricular pacing. In some examples, whether LPD 10A is operating in a sensing without pacing mode or in an atrio-ventricular synchronous pacing mode is controlled based on the detection of ventricular undersensing, as described in further detail below the respect to FIGS. 6A, 6B, and 7. In addition, in some examples, whether LPD 10A delivers pacing pulses to a patient in an atrio-ventricular synchronous pacing mode or an asynchronous ventricular pacing mode is controlled based on the detection of an atrial undersensing event, as described in further detail below.

As illustrated in FIG. 1, LPD 10A includes an outer housing 12, fixation times 14A-14D (collectively "fixation tines 14"), and electrodes 16A and 16B. Outer housing 12 is configured such that, e.g., has a size and form factor, that allows LPD 10A to be entirely implanted within a chamber of a heart, such as a right ventricle. As illustrated in FIG. 1, housing 12 may have a cylindrical (e.g., pill-shaped) form factor in some examples. Housing 12 may be hermetically sealed to prevent ingress of fluids into the interior of housing 12.

Fixation tines 14 extend from outer housing 12, and are configured to engage with cardiac tissue to substantially fix a position of housing 12 within a chamber of a heart, e.g., at or near an apex of a right ventricle. Fixation tines 14 are configured to anchor housing 12 to the cardiac tissue such that LPD 10A moves along with the cardiac tissue during cardiac contractions. Fixation tines 14 may be fabricated from any suitable material, such as a shape memory material (e.g., Nitinol). The number and configuration of fixation tines 14 illustrated in FIG. 1 is merely one example, and other numbers and configurations of fixation tines for anchoring an LPD housing to cardiac tissue are contemplated. Additionally, although LPD 10A includes a plurality of fixation tines 14 that are configured to anchor LPD 10A to cardiac tissue in a chamber of a heart, in other examples, LPD 10A may be fixed to cardiac tissue using other types of fixation mechanisms, such as, but not limited to, barbs, coils, and the like.

LPD 10A is configured to sense electrical activity of a heart, i.e., a cardiac electrogram ("EGM"), and deliver pacing pulses to a right ventricle, via electrodes 16A and 16B. Electrodes 16A and 16B may be mechanically connected to housing 12, or may be defined by a portion of housing 12 that is electrically conductive. In either case, electrodes 16A and 16B are electrically isolated from each other. Electrode 16A may be referred to as a tip electrode, and fixation tines 14 may be configured to anchor LPD 10A to cardiac tissue such that electrode 16A maintains contact with the cardiac tissue. Electrode 16B may be defined by a conductive portion of housing 12 and, in some examples, may define at least part of a power source case that houses a power source (e.g., a battery) of LPD 10A. In some examples, a portion of housing 12 may be covered by, or formed from, an insulative material to isolate electrodes 16A and 16B from each other and/or to provide a desired size and shape for one or both of electrodes 16A and 16B.

Outer housing 12 houses electronic components of LPD 10A, e.g., an electrical sensing module for sensing cardiac electrical activity via electrodes 16A and 16B, a sensor, and an electrical stimulation module for delivering pacing pulses via electrodes 16A and 16B. Electronic components may include any discrete and/or integrated electronic circuit components that implement analog and/or digital circuits capable of producing the functions attributed to an LPD described herein. Additionally, housing 12 may house a memory that includes instructions that, when executed by one or more processors housed within housing 12, cause LPD 10A to perform various functions attributed to LPD 10A herein. In some examples, housing 12 may house a communication module that enables LPD 10A to communicate with other electronic devices, such as a medical device programmer. In some examples, housing 12 may house an antenna for wireless communication. Housing 12 may also house a power source, such as a battery. The electronic components of LPD 10A are described in further detail below, with respect to FIG. 4.

Figure 2:
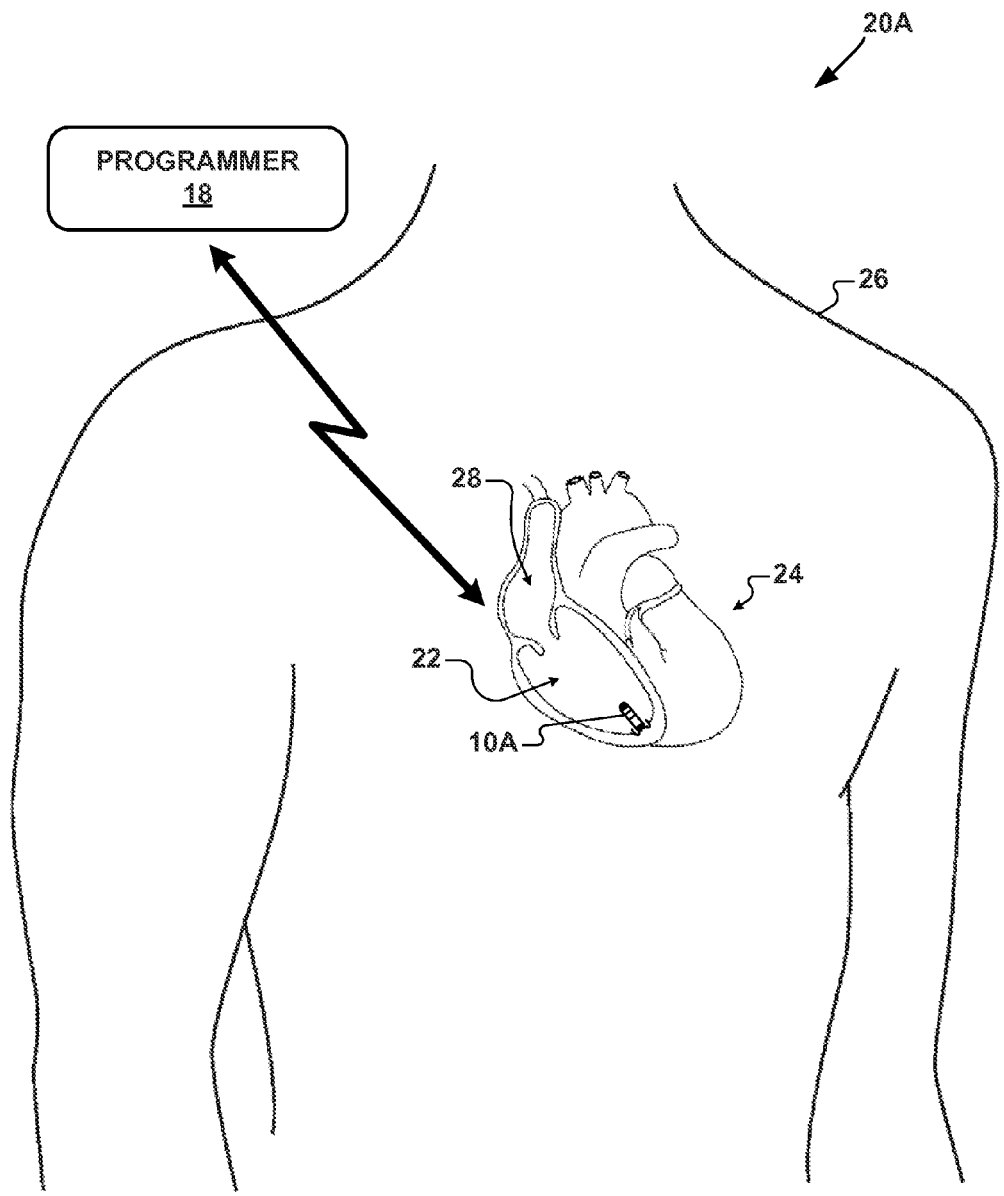
FIG. 2 is a conceptual diagram illustrating a leadless pacing system that comprises the example leadless pacing device of FIG. 1.

FIG. 2 is a conceptual diagram illustrating an example leadless pacing system 20A that comprises the example LPD 10A from FIG. 1. In the example of FIG. 2, LPD 10A is implanted within right ventricle 22 of heart 24 of patient 26. More particularly, LPD 10A is fixed or attached to the inner wall of the right ventricle 22 proximate to the apex of the right ventricle in the example of FIG. 2 via the fixation tines 14. In other examples, LPD 10A may be fixed to the inner wall of right ventricle 22 at another location, e.g., on the intraventricular septum or free-wall of right ventricle 22, or may be fixed to the outside of heart 24, e.g., epicardially, proximate to right ventricle 22. In other examples, LPD 10A may be fixed within, on, or near the left-ventricle of heart 24.

LPD 10A includes a plurality of electrodes that are affixed to, or are a portion of, the housing of LPD 10A, i.e., electrodes 16A and 16B. LPD 10A may be configured to sense electrical cardiac signals associated with depolarization and repolarization of heart 24, e.g., an EGM, via electrodes 16A and 16B. LPD 10A is also configured to deliver cardiac pacing pulses to right ventricle 22 via electrodes 16A and 16B. In some examples, LPD 10A may deliver the cardiac pacing pulses according to an atrio-ventricular synchronous pacing mode or an asynchronous ventricular pacing mode, depending on whether one or more undersensing events are detected.

LPD 10A is configured to detect a ventricular activation event in any suitable way. In some examples, a processing module of LPD 10A is configured to detect a ventricular activation event based on ventricular electrical activity (e.g., an R-wave), which may be indicative of an intrinsic depolarization of right ventricle 22. In addition to, or instead of, the ventricular electrical activity, the processing module is configured to detect a ventricular activation event based on the delivery of a pacing pulse to right ventricle 22. In yet other examples, the processing module may be configured to detect a ventricular activation event based on detection of a ventricular contraction, which may be detected based on heart sounds (e.g., the S1 heart sounds) sensed by a sensor of LPD 10A, or based on motion of the right ventricle (e.g., sensed by a motion sensor of LPD 10A or another device).

LPD 10A is configured to detect an atrial activation event in any suitable way. In some examples, LPD 10A is configured to detect an atrial activation event based on a mechanical contraction of right atrium 28, based on detection of an atrial depolarization within the electrical cardiac signal, or based on both the mechanical contraction and the atrial depolarization. LPD 10A may, for example, detect an atrial depolarization by at least detecting a P-wave, which represents atrial depolarization, within the electrical cardiac signal.

In some examples, LPD 10A may, at times, undersense atrial activation events. For example, the LPD 10A may be unable to reliably detect atrial depolarizations, e.g., due to the quality of the electrical signal sensed by electrodes 16A, 16B of LPD 10A, or the relatively small magnitude of the atrial depolarizations (e.g., small P-wave amplitude) within the sensed electrical cardiac signal. As described in greater detail below, in some examples, LPD 10A is configured to switch from an atrio-ventricular synchronous pacing mode to an asynchronous pacing mode in response to detecting an atrial undersensing event.

In contrast to LPD 10A, a dual chamber pacemaker that is electrically connected to leads that extend into right ventricle 22 and right atrium 28 of heart 24, LPD 10A (as well as other LPDs) may sense atrial activity with electrodes placed within right atrium 28. As a result, the amplitude of the P-wave of an electrical cardiac signal sensed by the dual chamber pacemaker (or other pacemaker with leads in right atrium 28) may be larger than the amplitude of the P-wave of an electrical cardiac signal sensed by LPD 10A. An electrical cardiac signal with larger P-wave amplitudes may result in fewer atrial undersensing events. Thus, a switch from an atrio-ventricular synchronous pacing mode to an asynchronous pacing mode in response to detecting an atrial undersensing event, as described herein with respect to LPDs, may not be applicable to a dual chamber pacemaker (or other pacemaker with leads in right atrium 28) or provide improved utility of the dual chamber pacemaker.

As illustrated in FIG. 2, LPD system 20A also includes a medical device programmer 18, which is configured to program LPD 10A and retrieve data from LPD 10A. Programmer 18 may be a handheld computing device, a desktop computing device, a networked computing device, etc. Programmer 18 may include a computer-readable storage medium having instructions that cause a processing module of programmer 18 to provide the functions attributed to programmer 18 in the present disclosure. LPD 10A may wirelessly communicate with programmer 18. For example, LPD 10A may transfer data to programmer 18 and may receive data from programmer 18. Programmer 18 may also wirelessly program and/or wirelessly charge LPD 10A.

Data retrieved from LPD 10A using programmer 18 may include electrical cardiac signals stored by LPD 10A that indicate the electrical activity of heart 24, generated undersensing indications and marker channel data that indicates the occurrence and timing of sensing, diagnosis, and therapy events associated with LPD 10A, e.g., detection of atrial and ventricular depolarizations and delivery of pacing pulses. Data transferred to LPD 10A using programmer 18 may include, for example, operational programs for LPD 10A that cause LPD 10A to operate as described herein. As examples, data transferred to LPD 10A using programmer 18 may include lengths of any AV intervals, lengths of any VV intervals, atrial contraction detection delay periods, ventricular activation event detection windows, atrial activation event detection windows, and offsets for determining modified atrial activation event detection windows, which are each described in further detail below. It may also include any threshold values, such as for detecting atrial and/or ventricular contractions, for detecting an undersensing event (e.g., based on a number of undersensing indications), or programming used by LPD 10A to determine such values based on determined parameters of heart 24, patient 26, or LPD 10A.

Figure 3A:
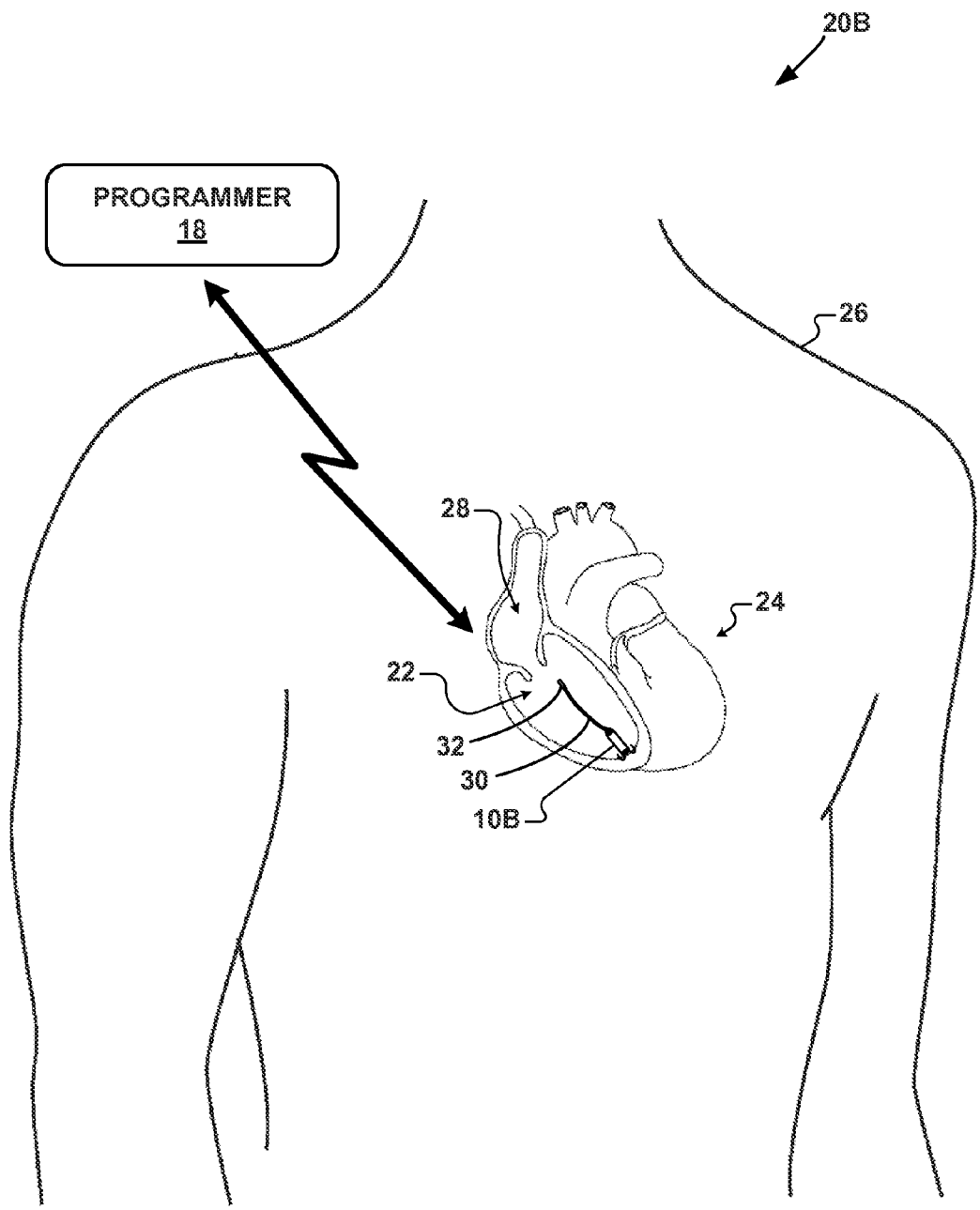
FIG. 3A is a conceptual diagram illustrating another example leadless pacing system that comprises a leadless pacing device configured to deliver atrio-ventricular synchronous pacing and asynchronous ventricular pacing.
Figure 3B:
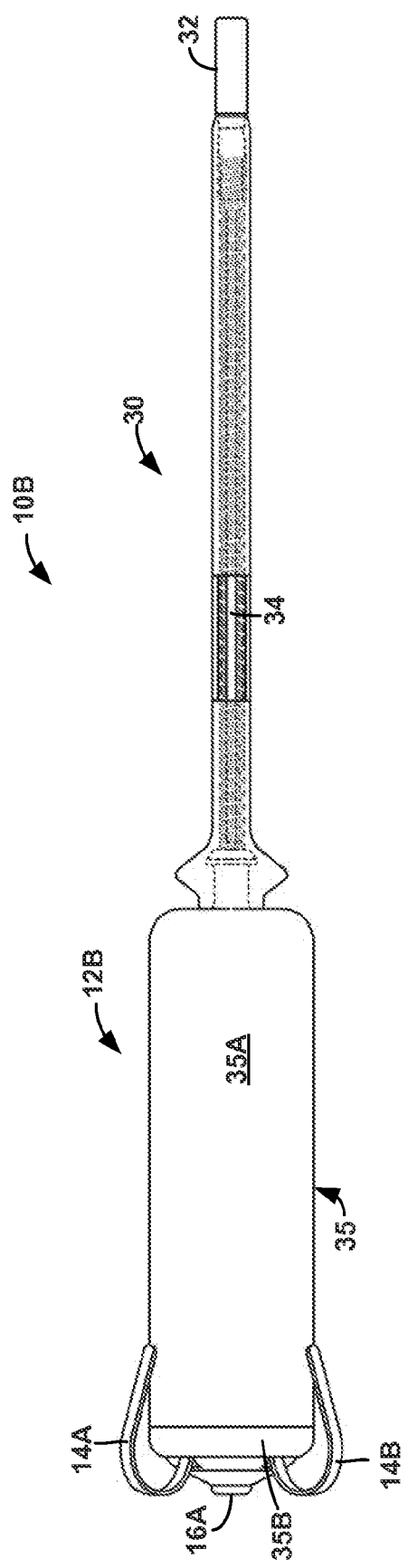
FIG. 3B is a conceptual diagram illustrating the leadless pacing device of FIG. 3A.

FIG. 3A is a conceptual diagram illustrating another example leadless pacing system 20B that comprises another example LPD 10B configured to operate in a sensing without pacing mode and an atrio-ventricular synchronous pacing mode in some examples. In addition, or instead, in some examples, as with LPD 10A, LPD 10B is configured to deliver either atrio-ventricular synchronous pacing or asynchronous ventricular pacing based on a detection of one or more undersensing events. FIG. 3B illustrates LPD 10B in further detail. Leadless pacing system 20B and LPD 10B may be substantially the same as leadless pacing system 20A and LPD 10A described above with respect to FIGS. 1 and 2. Unlike LPD 10A, however, LPD 10B is coupled to a sensing extension 30 that includes an electrode 32. In some examples, sensing extension 30 may include one or more additional electrodes having the same polarity as electrode 32. Although not illustrated in FIGS. 3A and 3B, LPD 10B may include an electrode 16A but may not include electrode 16B, as described above with respect to LPD 10A and FIG. 1.

Electrode 32 is electrically connected to electronics within a housing of LPD 10B (e.g., an electrical sensing module and a stimulation module) via an electrical conductor 34 of sensing extension 30. In some examples, electrical conductor 34 is connected to the electronics via an electrically conductive portion 36A of outer housing 36 of LPD 12B, which may correspond to electrode 16B of LPD 10A (FIG. 1), but may be substantially completely insulated (e.g., completely electrically insulated or nearly completely electrically insulated). Substantially completely electrically insulating conductive portion 36A of housing 36 may allow an electrical sensing module of LPD 10B to sense electrical cardiac activity with electrode 32 of sensing extension 30, rather than conductive portion 36A of housing 36. This may help improve the magnitude of the atrial depolarization present within an electrical cardiac signal sensed via LPD 10B, particularly relative to the examples in which electrodes 16A, 16B are affixed to, or are a portion of, the housing of LPD 10A (FIG. 1).

Additionally, as shown in FIGS. 3A and 3B, sensing extension 30 extends away from LPD 10B, which enables electrode 32 to be positioned relatively close to right atrium 28. As a result, an electrical cardiac signal sensed by LPD 10B via electrodes 16A (FIG. 1) and 32 may include a higher amplitude far-field atrial depolarization signal than an electrical cardiac signal sensed by LPD 10A via electrodes 16A and 16B (FIG. 1). In this way, sensing extension 30 may facilitate detection of atrial depolarizations when LPD 10B is implanted in right ventricle 22. In some examples, sensing extension 30 is sized to be entirely implanted within right ventricle 22. In other examples, sensing extension 30 is sized to extend into right atrium 28.

Despite sensing extension 30, LPD 10B may, at times, be unable to detect depolarizations of right atrium 28, e.g., due to reduced electrical cardiac signal quality. Reduced electrical cardiac signal quality may include reduced amplitude of the atrial component of the electrical cardiac signal and/or increased noise, which may cause LPD 10B to undersense atrial events when LPD 10B is implanted in right ventricle 22. Reduced electrical cardiac signal quality may be caused by, for example, movement of sensing extension 30 relative to right atrium 28, which may be caused by posture or activity of patient 26, or other conditions of patient 26, heart 24, and/or LPD 10B. In order to help provide responsive pacing therapy, LPD 10B may be configured to deliver pacing pulses to right ventricle 22 in accordance with either the atrio-ventricular synchronous pacing mode or the asynchronous ventricular pacing made, based on detection of an atrial undersensing event.

While the remainder of the disclosure primarily refers to LPD 10A, the description of LPD 10A also applies to LPD 10B, as well as other LPDs configured to provide both atrio-synchronous ventricular pacing and asynchronous ventricular pacing.

Figure 4:
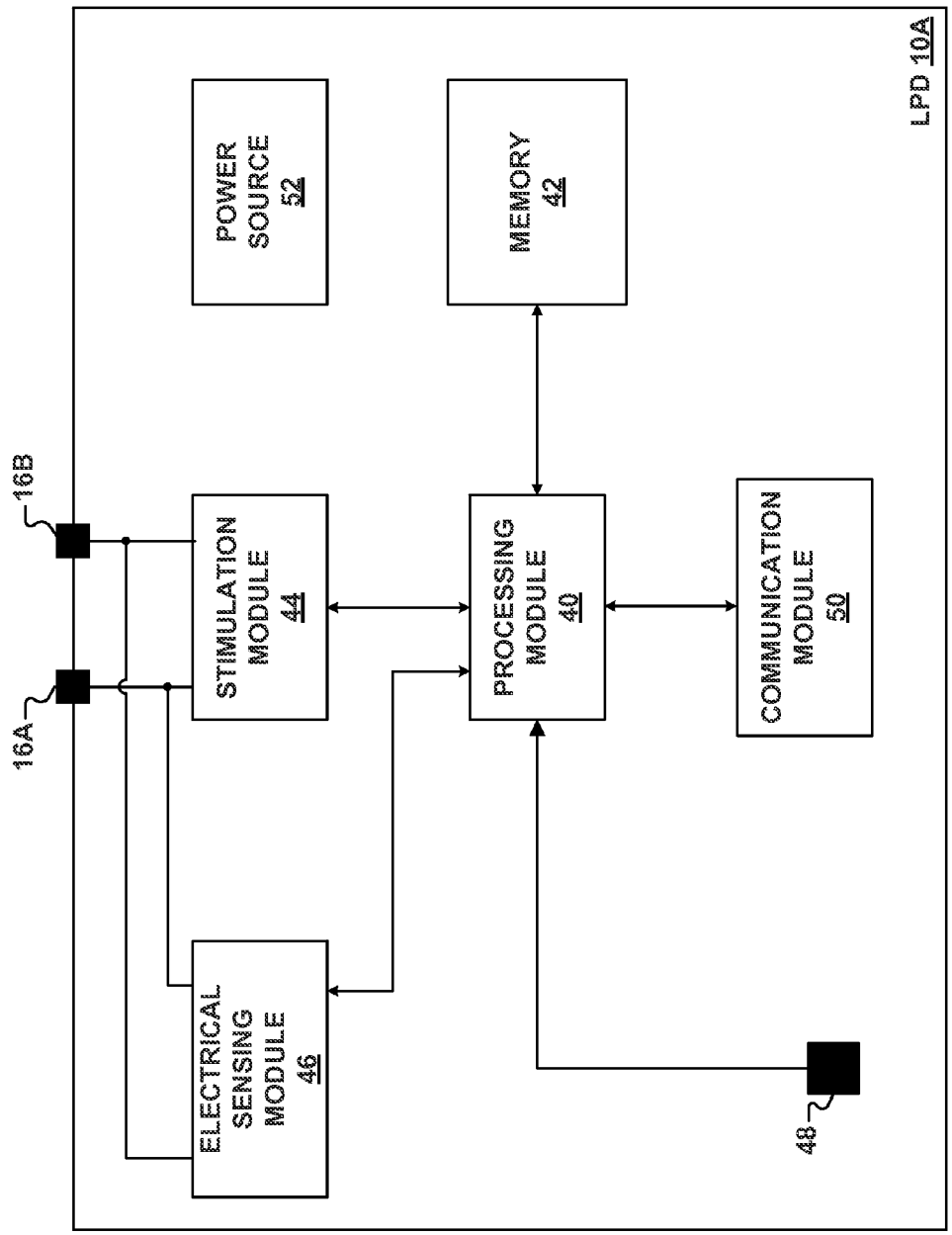
FIG. 4 is a functional block diagram illustrating an example configuration of the example leadless pacing device of FIG. 1.

FIG. 4 is a functional block diagram illustrating an example configuration of an LPD 10A configured to deliver atrio-ventricular synchronous pacing or asynchronous ventricular pacing based on a detection of an atrial sensing event. LPD 10B of FIGS. 3A and 3B may have a similar configuration as LPD 10A. However, electrode 16B of LPD 10A may be replaced by electrode 32 of LPD 10B, which may be positioned a greater distance away from electrode 16A and LPD 10B, as described above with respect to FIGS. 3A and 3B.

LPD 10A includes processing module 40, memory 42, stimulation module 44, electrical sensing module 46, sensor 48, communication module 50, and power source 52. Power source 52 may include a battery, e.g., a rechargeable or non-rechargeable battery.

Modules included in LPD 10A represent functionality that may be included in LPD 10A of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 40 may include any one or more of a microprocessor, a controller, a digital signal processor (DSP), an application specific integrated circuit (ASIC), a field-programmable gate array (FPGA), or equivalent discrete or integrated logic circuitry. In some examples, processing module 40 includes multiple components, such as any combination of one or more microprocessors, one or more controllers, one or more DSPs, one or more ASICs, or one or more FPGAs, as well as other discrete or integrated logic circuitry. Additionally, although illustrated as separate functional components in FIG. 4, some or all of the functionality attributed to stimulation module 44, electrical sensing module 46, and communication module 50 may implemented in the one or more combination of one or more microprocessors, one or more controllers, one or more DSPs, one or more ASICs, one or more FPGAs, and/or other discrete or integrated logic circuitry that implements processing module 40.

Processing module 40 may communicate with memory 42. Memory 42 may include computer-readable instructions that, when executed by processing module 40, cause processing module 40 and any other modules of LPD 10A to perform the various functions attributed to them herein. Memory 42 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device.

Stimulation module 44 and electrical sensing module 46 are electrically coupled to electrodes 16A, 16B. Processing module 40 is configured to control stimulation module 44 to generate and deliver pacing pulses to heart 24 (e.g., right ventricle 22 in the example shown in FIG. 2) via electrodes 16A, 16B. In addition, processing module 40 is configured to control electrical sensing module 46 to monitor an electrical signal from electrodes 16A, 16B in order to monitor electrical activity of heart 24. Electrical sensing module 46 may include circuits that acquire an electrical signal from electrodes 16A, 16B, as well as circuits to filter, amplify, and otherwise process the electrical signal. The electrical signal includes intrinsic cardiac electrical activity, such as depolarizations and repolarizations of the ventricles and depolarizations of the atria, and may be referred to as an electrical cardiac signal or a cardiac electrogram signal. Electrical sensing module 46 detects ventricular depolarizations, or ventricular activation events, within the electrical cardiac signal and detects atrial depolarizations, or atrial activation events, within the electrical cardiac signal.

In some examples, LPD 10A also includes sensor 48. In some examples, sensor 48 comprises one or more accelerometers. In some examples, sensor 48 comprises a plurality of accelerometers, e.g., three accelerometers, each of which is oriented to detect motion in the direction of a respective axis or vector. The axes or vectors may be orthogonal. In other examples, sensor 48 may comprises one or more different sensors that generate a signal as a function of motion, instead of or in addition to the one or more accelerometers, such as gyros, mercury switches, or bonded piezoelectric crystals. In other examples, sensor 48 may be a pressure sensor instead of one or more accelerometers.

Communication module 50 may include any suitable hardware (e.g., an antenna), firmware, software, or any combination thereof for communicating with another device, such as programmer 18 (FIGS. 2 and 3) or a patient monitor. Under the control of processing module 40, communication module 50 may receive downlink telemetry from and send uplink telemetry to other devices, such as programmer 18 or a patient monitor, with the aid of an antenna included in communication module 50.

Memory 42 may include data recorded by LPD 10A, e.g., electrical cardiac signals, heart rates, information regarding detection of atrial sensing events or undersensing events, undersensing indications, ventricular pacing efficacy, and the like. Under the direction of processing module 40, communication module 50 may transfer data recorded by LDP 10A to another device, such as programmer 18. Memory 42 may also store programming data received by processing module 40 from another device, such as programmer 18, via communication module 50. The programming data stored in memory 42 may include, as examples, lengths of any AV intervals, lengths of any VV intervals, atrial contraction detection delay periods, and atrial or ventricular activation event detection windows described herein. The programming data stored in memory 42 may additionally or alternatively include any threshold values described hereafter, such as for detecting atrial and/or ventricular contractions, determining whether pacing is efficacious, or determining whether atrio-ventricular synchronous pacing should be suspended in favor of asynchronous pacing. The programming data stored in memory 42 may additionally or alternatively include data used by processing module 40 to determine any values described herein, e.g., based determined parameters of heart 24, patient 26, or LPD 10A.

Figure 5:
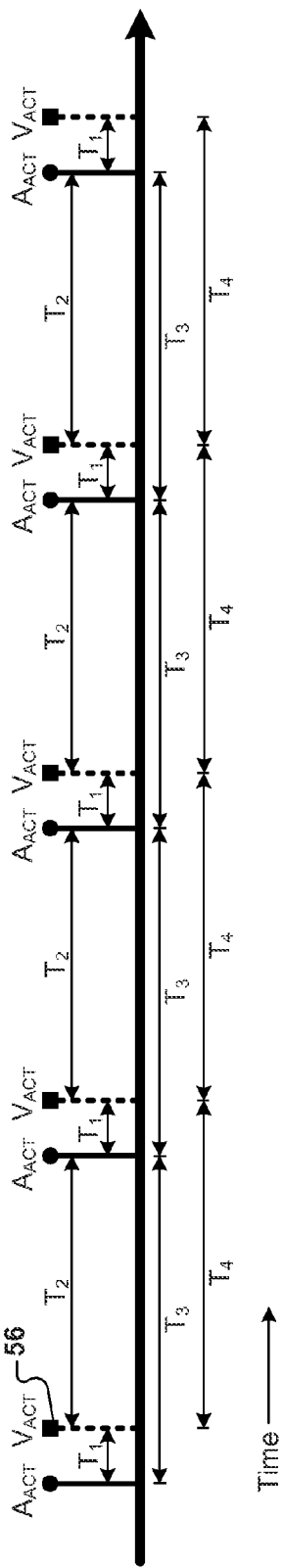
FIG. 5 is a timing diagram illustrating normal conduction timing in a patient.

FIG. 5 is a timing diagram illustrating normal conduction timing in a patient. The amount of time between an atrial activation event (paced or sensed) and a subsequent ventricular activation event may be generally referred to herein as an "$A_{ACT}$-$V_{ACT}$ interval." In FIG. 5, the $A_{ACT}$-$V_{ACT}$ interval has a consistent value of T1, while the intervals between consecutive atrial events (i.e., the A-A interval) consistently have a value of T3. The interval between a ventricular activation event $V_{ACT}$ and a subsequent atrial activation event $A_{ACT}$ has a consistent value of T2, and the intervals between consecutive ventricular activation events (i.e., the VV interval) may consistently have a value of T4.

Figure 6A:
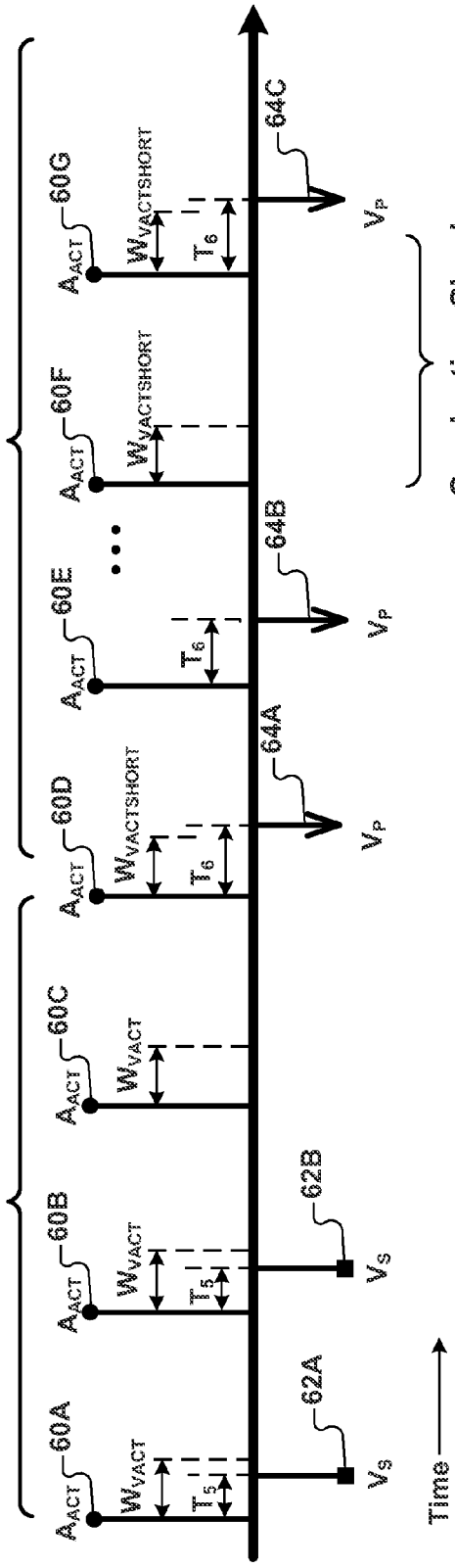
FIG. 6A is a timing diagram illustrating an example technique for controlling a leadless pacing device to switch from a sensing without pacing mode to an atrio-ventricular synchronous pacing mode.

FIG. 6A is a timing diagram illustrating an example technique for controlling LPD 10A (or another LPD) implanted in right ventricle 22 to switch from a sensing without pacing mode to an atrio-ventricular synchronous pacing mode in response to detecting ventricular undersensing. The timing diagram also illustrates an example technique for delivering atrio-ventricular synchronous pacing based on detection of an atrial activation event. An activation of an atrium may be an intrinsic or paced depolarization of the atrium, or a mechanical contraction of the atrium. Thus, processing module 40 may identify activation of an atrium by determining that electrical sensing module 46 detected an intrinsic depolarization of the atrium (e.g., a far field P-wave), by determining that another device (e.g., another LPD implanted in the atrium) delivered a pacing pulse to the atrium, or by detecting mechanical contraction of the atrium.

In some examples, in a sensing without pacing mode, processing module 40 may detect atrial activation events $A_{ACT}$, e.g., in an electrical cardiac signal sensed by electrical sensing module 46 (FIG. 4), as well as ventricular sense events $V_S$ (e.g., R-waves), e.g., in the sensed electrical cardiac signal. The ventricular sense event $V_S$ may indicate intrinsic depolarization of the ventricle (e.g., the right ventricle 22) in which LPD 10A is implanted. Processing module 40 may determine whether a ventricular sense event $V_S$ is detected within a ventricular event detection window $W_{VACT}$ that begins at an atrial activation event $A_S$. This may indicate that heart 24 is exhibiting normal intrinsic conduction.

In some examples, processing module 40 determines the duration of the ventricular event detection window $W_{VACT}$ based on the stored data that indicates the interval between consecutive atrial activation events (i.e., the A-A interval) for a predetermined number of most recent cardiac cycles (e.g., one to 12 beats). This historic A-A interval data may be stored by memory 42 or a memory of another device. In some examples, the duration of the ventricular event detection window $W_{VACT}$ may be one of: the mean A-A interval of the stored A-A intervals, the median A-A interval of the stored A-A intervals, the greatest A-A interval of the stored A-A intervals, the shortest A-A interval of the stored A-A intervals, or the most recent A-A interval of the stored A-A intervals. As another example, the duration of the ventricular event detection window $W_{VACT}$ may be a predetermined percentage of the stored A-A intervals, such as 30% to about 75% (e.g., about 50%) of the mean or median A-A interval for the last one to 12 beats.

In addition, or instead, the duration of the ventricular event detection window $W_{VACT}$ may be selected by a clinician and may be independent of the historic A-A interval data for the patient. For example, in some examples, the duration of the ventricular event detection window $W_{VACT}$ is preprogrammed to be a fixed duration between about 300 milliseconds (ms) to about 700 ms, such as about 500 ms. Processing module 40 may receive the ventricular event detection window $W_{VACT}$ from the clinician via, e.g., a medical device programmer that is configured to communicate with LPD 10A.

In yet other examples, processing module 40 determines the duration of the ventricular event detection window $W_{VACT}$ based on the stored data that indicates the interval between consecutive atrial events (i.e., the A-A interval) for a certain number of most recent cardiac cycles and a preprogrammed duration. For example, processing module 40 may determine a first ventricular event detection window $W_{VACT}$ based on the stored A-A interval data, e.g., using the techniques described above, and may select the duration of the ventricular event detection window $W_{VACT}$ to be the smaller of the first ventricular event detection window $W_{VACT}$ and a fixed, programmed duration. In this way, at relatively slow heart rates, processing module 40 use the fixed, programmed duration as the ventricular event detection window $W_{VACT}$, and at higher heart rates, the duration that is based on the actual cardiac activity of patient 12 may be used.

In response to determining that, for a particular cardiac cycle, a ventricular sense event $V_S$ is detected within the ventricular event detection window $W_{VACT}$, processing module 40 may continue operating LPD 10A in the sensing without pacing mode for at least the next cardiac cycle. For example, as shown in FIG. 6A, processing module 40 detects atrial activation event 60A and a ventricular sense event 62A that is detected within a time period $T_5$ of atrial activation event 60A, the duration of time period $T_5$ being less than the duration of ventricular event detection window $W_{VACT}$. Atrial activation event 60A and ventricular sense event 62A are part of the same cardiac cycle. Thus, processing module 40 maintains the sensing without pacing mode for the next cardiac cycle. Processing module 40 detects a subsequent normal cardiac cycle in which ventricular sense event 62B is detected by processing module 40 within a ventricular event detection window $W_{VACT}$ of atrial activation event 60B.

During a next cardiac cycle in the example shown in FIG. 6A, however, processing module 40 does not detect a ventricular sense event within a ventricular event detection window $W_{VACT}$ of atrial activation event 60C. Rather than controlling stimulation module 44 (FIG. 4) to deliver a pacing pulse to right ventricle 22 of heart 24 of patient 12 within the same cardiac cycle as atrial activation event 60C, however, processing module 40 may hold off on the delivery of ventricular pacing for at least one cardiac cycle. This may permit processing module 40 to, for example, sense the intrinsic conduction of heart 24 and determine whether heart 24 returns to a normal cardiac rhythm without the aid of pacing therapy. In this way, processing module 40 may be configured to control pacing therapy to favor intrinsic conduction.

In the example shown in FIG. 6A, in order to determine whether heart 24 returns to a normal cardiac rhythm without the aid of pacing therapy, processing module 40 determines whether a ventricular sense event $V_S$ is detected within the ventricular event detection window $W_{VACT}$ of an atrial activation event 60D of a subsequent cardiac cycle (immediately after the cardiac cycle in which the ventricular sense event was not detected within the ventricular event detection window $W_{VACT}$). In response to detecting a ventricular sense event $V_S$ within the ventricular event detection window $W_{VACT}$ of an atrial activation event 60D of a subsequent cardiac cycle, processing module 40 may continue to operate LPD 10A in a sensing without pacing mode.

In some examples, processing module 40 may maintain the ventricular event detection window $W_{VACT}$ for the next cardiac cycle. In other examples, however, as shown in FIG. 6A, processing module 40 may shorten the ventricular event detection window $W_{VACT}$ in the cardiac cycle following the cycle in which the ventricular sense event was not detected (e.g., in which a beat was dropped). In the example shown in FIG. 6A, the cycle in which the ventricular sense event was not detected is the cardiac cycle including atrial activation event 60C. Shortening the ventricular event detection window $W_{VACT}$ to be a smaller duration ventricular event detection window $W_{VACTSHORT}$ in the cardiac cycle following the cycle in which the ventricular sense event was not detected may help provide more responsive cardiac pacing therapy because shortening the ventricular event detection window $_T$ may result in a more timely ventricular pacing pulse $V_P$ in the subsequent cardiac cycle. In some examples, ventricular event detection window $W_{VACTSHORT}$ is about 70 ms to about 110 ms, such as about 80 ms in the cardiac cycle including atrial activation event 60D and/or in the cardiac cycle including atrial activation event 60E.

In the example shown in FIG. 6A, however, processing module 40 does not detect a ventricular sense event $V_S$ within the shortened ventricular event detection window $W_{VACTSHORT}$ that begins at atrial activation event 60D. In response, processing module 40 switches LPD 10A from the sensing without pacing mode to an atrio-ventricular synchronous pacing mode. According to an example technique for delivering atrio-ventricular synchronous pacing shown in FIG. 6A, after processing module 40 determines that an intrinsic ventricular sense event $V_S$ is not detected within a shortened ventricular event detection window $W_{VACTSHORT}$ that begins at atrial activation event 60D, processing module 40 may control stimulation module 44 to deliver ventricular pacing pulse $V_P$ 64A to a ventricle (e.g., right ventricle 22) of heart 24 a time period $T_6$ after a detected atrial activation event $A_{ACT}$. In the example shown in FIG. 6A, time period $T_6$ has a duration greater than or equal to the shortened ventricular event detection window $W_{VACTSHORT}$, and may be less than or equal to ventricular event detection window $W_{VACT}$. In addition, in the example shown in FIG. 6A, processing module 40 controls stimulation module 44 to deliver the ventricular pacing pulse $V_P$ 64A about 80 milliseconds after atrial activation event 60D. Other time intervals may also be used in other examples.

Processing module 40 may control the duration of time $T_6$ between the detection of atrial activation $A_S$ and the delivery of the next ventricular pacing pulse $V_P$. In some examples, processing module 40 selects the duration of time period $T_6$ based on the $A_{ACT}$-$V_S$ interval of two or more prior cardiac cycles (e.g., two cardiac cycles, three cardiac cycles, or more), which may be the cardiac cycles immediately preceding the first cardiac cycle in which the ventricular sense event was not sensed. For example, the duration of time period $T_6$ may be equal to the average $A_{ACT}$-$V_S$ interval of the two or more prior cardiac cycles. The average $A_{ACT}$-$V_S$ interval may be better representative of the current heart rate of patient 26 than, for example, a preprogrammed atrio-ventricular synchronous pacing interval ($A_{ACT}$-$V_P$), which affects the pacing interval. In this way, controlling the delivery of ventricular pacing pulse $V_P$ relative to an atrial activation event $A_{ACT}$ based on the average $A_{ACT}$-$V_S$ interval of the two or more preceding cardiac cycles may help smooth the heart rate of patient 26, particularly when compared to the delivery of atrio-ventricular synchronous pacing using a preprogrammed atrio-ventricular synchronous pacing interval ($A_{ACT}$-$V_P$).

In a next cardiac cycle, processing module 40 detects an atrial activation event 60E, determines whether a ventricular sense event is detected within a shortened ventricular event detection window $W_{VACTSHORT}$ that begins at atrial activation event 60E, and, in response to determining the ventricular sense event as not detected within the shortened ventricular event detection window $W_{VACTSHORT}$ or within a predetermined AV interval, processing module 40 controls stimulation module 44 to deliver ventricular pacing pulse $V_P$ 64A to a ventricle (e.g., right ventricle 22) of heart 24 a time period $T_6$ after the detected atrial activation event $A_{ACT}$ 60E. However, if processing module 40 detects the ventricular sense event within the shortened ventricular event detection window $W_{VACTSHORT}$ or the AV interval, then processing module 40 may not control stimulation module 44 to deliver ventricular pacing in that particular cardiac cycle.

In some examples, once processing module 40 switches to the atrio-ventricular synchronous pacing mode, processing module 40 may apply a different ventricular event detection window $W_{VACTSHORT}$, which may be preprogrammed and associated with the atrio-ventricular synchronous pacing mode. For example, the ventricular event detection window $W_{VACT}$ applied during the atrio-ventricular synchronous pacing mode may be about 80 ms to about 300 ms such as about 130 ms, although other windows may also be used. Thus, in some examples of the technique shown in FIG. 6A, the ventricular event detection window $W_{VACTSHORT}$ used by processing module 40 in the cardiac cycle including atrial activation event 60D may differ from the one used during the cardiac cycle including atrial activation event 60E. As a result, in some examples, the time periods $T_6$ may differ in the cardiac cycles including events 60D, 60E.

In some examples, the AV interval may be equal to the ventricular event detection window $W_{VACT}$ discussed with reference to FIGS. 6A, 6B, and 7. In other examples, the AV interval may be less than the ventricular event detection window $W_{VACT}$. In yet other examples, the AV interval may be greater than the ventricular event detection window $W_{VACT}$. In some examples, the AV interval is preprogrammed, e.g., selected by a clinician. Example AV intervals include, for example, about 80 ms to about 300 ms range, such as about 130 ms, although other AV intervals may be used in other examples.

During operation in the atrio-ventricular synchronous pacing mode, processing module 40 may periodically perform an intrinsic conduction check to determine whether heart 24 has returned to normal intrinsic conduction. For example, processing module 40 may control stimulation module 44 to withhold ventricular pacing ($V_P$) for at least one cardiac cycle (e.g., one cardiac cycle, two cardiac cycles, or three or more cardiac cycles) in order to determine whether an intrinsic ventricular sense event $V_S$ is detected within a ventricular event detection window $W_{VACT}$ of an atrial activation event $A_{ACT}$.

In the example shown in FIG. 6A, processing module 40 does not detect a ventricular activation event $V_S$ within the ventricular event detection window $W_{VACTSHORT}$ of atrial activation event $A_{ACT}$ 60F or within the ventricular event detection window $W_{VACTSHORT}$ of atrial activation event $A_{ACT}$ 60G. In response to making this determination, processing module 40 may continue to control stimulation module 44 deliver ventricular pacing pulses to right ventricle 22 in the atrio-ventricular synchronous pacing mode. As shown in FIG. 6A, in this mode, processing module 40 may control stimulation module 44 to deliver ventricular pacing pulse $V_P$ 64C to patient 26 following the atrial activation event $A_{ACT}$ 60G of a subsequent cardiac cycle.

In examples in which processing module 40 detects an intrinsic ventricular sense event $V_S$ within the ventricular event detection window $W_{VACTSHORT}$ that begins at a respective atrial activation event $A_{ACT}$ 60E, processing module 40 may switch back LPD 10A to the sensing without pacing mode. In other examples, processing module 40 may switch LPD 10A to the sensing without pacing mode in response to determining that, for a predetermined threshold number (e.g., stored by memory 42) of consecutive cardiac cycles, an intrinsic ventricular sense event $V_S$ is detected within the ventricular event detection window $A_{ACT}$ of a respective atrial activation event $A_{ACT}$. The threshold number of cardiac cycles may be, for example, two, three, four, or more.

In addition, in some examples, processing module 40 may switch LPD 10A to the sensing without pacing mode in response to determining intrinsic conduction was observed during an intrinsic conduction check. In some examples, to perform the intrinsic conduction check, processing module 40 temporarily places LPD 10A in a sensing without pacing mode for at least one cardiac cycle (e.g., one cardiac cycle, or two cardiac cycles). In response to determining intrinsic conduction was observed during at least one cardiac cycle, processing module 40 may control LPD 10A to stay in the sensing without pacing mode.

Processing module 40 may perform the intrinsic conduction check at any suitable interval, which may remain the same or may increase over time. For example, after switching to the atrio-ventricular synchronous pacing mode, processing module 40 may perform the conduction checks at progressive time intervals that increase over time. As an example, one minute after switching LPD 10A to the atrio-ventricular synchronous pacing mode, processing module 40 may perform an intrinsic conduction test. If no intrinsic conduction is tested, then processing module 40 may continue operating LPD 10A in the atrio-ventricular synchronous pacing mode, and perform an intrinsic conduction check two minutes after the first check. If no intrinsic conduction is detected at that point, then processing module 40 may continue operating LPD 10A in the atrio-ventricular synchronous pacing mode and perform another intrinsic conduction check four minutes after the second check. This may go on with any suitable progressive time interval.

Figure 6B:
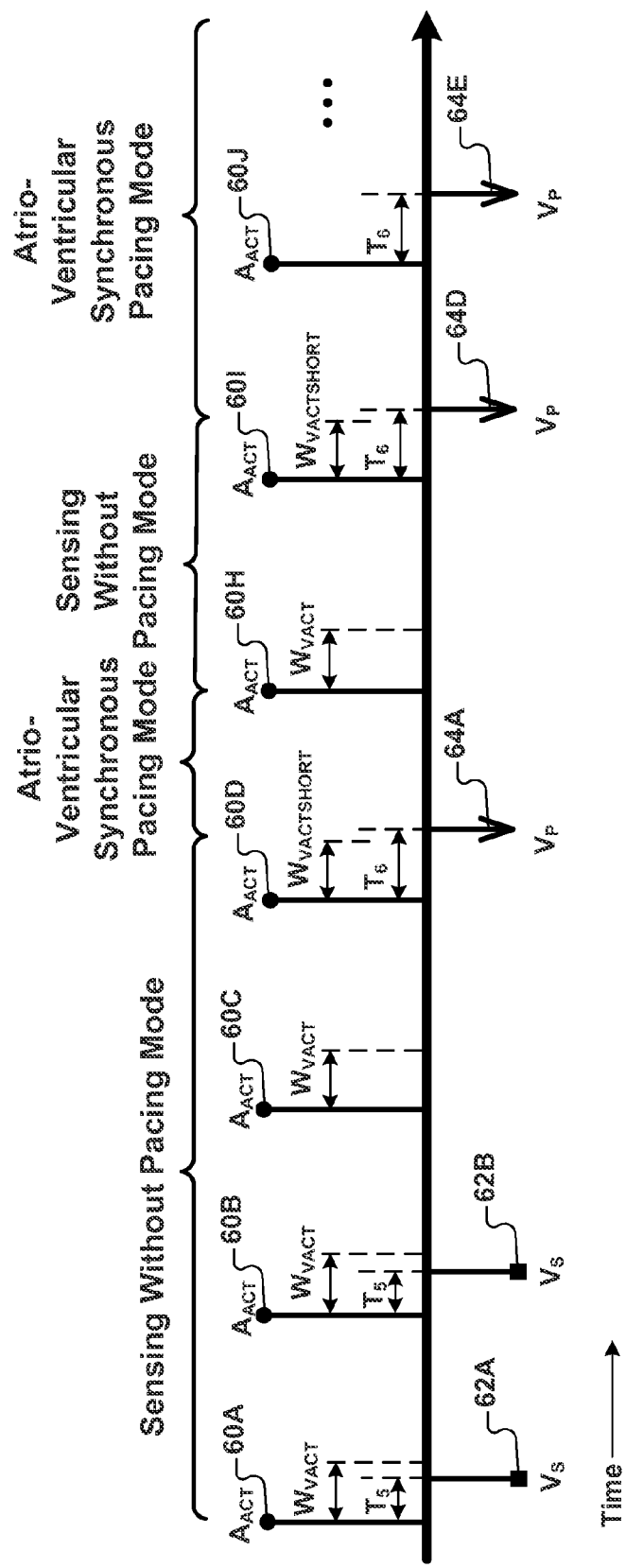
FIG. 6B is a timing diagram illustrating another example technique for controlling a leadless pacing device to switch from a sensing without pacing mode to an atrio-ventricular synchronous pacing mode.

FIG. 6B is a timing diagram illustrating another example technique for controlling LPD 10A (or another LPD) implanted in right ventricle 22 to switch from a sensing without pacing mode to an atrio-ventricular synchronous pacing mode in response to detecting ventricular undersensing. As with the technique described with respect to FIG. 6A, processing module 40 controls LPD 10A to switch from a sensing without pacing mode, in which no pacing therapy is delivered to heart 24 of patient 26, to an atrio-ventricular synchronous pacing mode in response to determining that, for one or more cardiac cycles, a ventricular sense event was not detected within a ventricular event detection window $W_{VACT}$ of an atrial activation event. For example, in FIG. 6B, processing module 40 does not detect a ventricular sense event within a ventricular event detection window $W_{VACT}$ of atrial activation event 60C. In that cardiac cycle including atrial activation event 60C, processing module 40 may hold off on the delivery of ventricular pacing for at least one cardiac cycle. Thus, as shown in FIG. 6B, no ventricular pacing pulse follows atrial activation event 60C.

As with the technique described with respect to FIG. 6A, processing module 40 does not detect a ventricular sense event $V_S$ within the shortened ventricular event detection window $W_{VACTSHORT}$ that begins at atrial activation event 60D and, in response, controls LPD 10A to deliver a pacing pulse $V_P$ 64A in accordance with an atrio-ventricular synchronous pacing mode. In contrast to the technique described with respect to FIG. 6A, however, in the example shown in FIG. 6B, processing module 40 does not control LPD 10A to remain in the atrio-ventricular synchronous pacing mode after delivering the pacing pulse $V_P$ 64A. Instead, processing module 40 controls LPD 10A to revert (e.g., switch) back to the sensing without pacing mode in which LPD 10A does not deliver any pacing therapy to patient 26.

As shown in FIG. 6B, after LPD 10A delivers pacing pulse $V_P$ 64A, processing module 40, while LPD 10A is in a sensing without pacing mode, detects an atrial activation event 60H and determines whether a ventricular sense event $V_S$ occurs within the shortened ventricular event detection window $W_{VACTSHORT}$ that begins at atrial activation event 60H. In the example shown in FIG. 6B, however, processing module 40 does not detect a ventricular sense event $V_S$ within the shortened ventricular event detection window $W_{VACTSHORT}$. However, because processing module 40 is controlling LPD 10A in accordance with a sensing without pacing mode, processing module 40 does not control stimulation module 44 to deliver a ventricular pacing pulse in response to determining the ventricular sense event $V_S$ was not detected within the shortened ventricular event detection window $W_{VACTSHORT}$ that begins at atrial activation event 60H. In this way, LPD 10A may drop a beat. Instead, processing module 40 may generate an undersensing indication, e.g., by incrementing an undersensing counter, in response to determining the ventricular sense event $V_S$ was not detected within the shortened ventricular event detection window $W_{VACTSHORT}$ that begins at atrial activation event 60H. Processing module 40 may then, in accordance with the sensing without pacing mode, detect a subsequent atrial activation event 60I and determine whether a ventricular sense event $V_S$ is detected within the shortened ventricular event detection window $W_{VACTSHORT}$ that begins at atrial activation event 60I.

According to the example technique shown in FIG. 6B, after processing module 40 determines that an intrinsic ventricular sense event $V_S$ is not detected within a shortened ventricular event detection window $W_{VACTSHORT}$ that begins at atrial activation event 60I, processing module 40 may control stimulation module 44 to deliver ventricular pacing pulse $V_P$ 64D to a ventricle (e.g., right ventricle 22) of heart 24 a time period $T_6$ after atrial activation event 60I. Processing module 40 may also generate an undersensing indication, e.g., by incrementing an undersensing counter.

In the example shown in FIG. 6B, processing module 40 implements an "X of Y" style counter, where "X" may be four undersensing indications and "Y" may be four, five, six, or more in some examples. In other examples, "X" may indicate the number of "skipped beats," e.g., the number of cardiac cycles in which a ventricular event, whether sensed or paced, was not detected. Thus, in some examples, "X" may be two undersensing indications and "Y" may be three, four, five, six, or more in some examples, e.g., four.

After processing module 40 increments the counter in response to determining that the ventricular sense event $V_S$ was not detected within the shortened ventricular event detection window $W_{VACTSHORT}$ that begins at atrial activation event 60I, processing module 40 may determine that counter indicates the "X" number of undersensing indications out of the "Y" number of cardiac cycles was detected. Accordingly, in response, processing module 40 may switch LPD 10A to the atrio-ventricular synchronous pacing mode indefinitely, e.g., until a conduction check indicates intrinsic conduction is detected or until another mode change is made (e.g., until processing module 40 determines a switch to an asynchronous pacing mode of LPD 10A would be desirable). Unlike in the cardiac cycle including atrial activation event 60D, processing module 40 may not revert LPD 10A back to a sensing without pacing mode of operation after LPD 10A delivers the ventricular pacing pulse 64D. Rather, processing module 40 may control stimulation module 44 to continue to deliver ventricular pacing pulses in accordance with the atrio-ventricular synchronous pacing mode.

For example, after switching to LPD 10A to the atrio-ventricular synchronous pacing mode, processing module 40 may detect an atrial activation event 60J and determine whether a ventricular sense event is detected within a shortened ventricular event detection window $W_{VACTSHORT}$ that begins at atrial activation event 60J. In response to determining the ventricular sense event as not detected within the shortened ventricular event detection window $W_{VACTSHORT}$ or within a predetermined AV interval, processing module 40 controls stimulation module 44 to deliver ventricular pacing pulse $V_P$ 64E to a ventricle (e.g., right ventricle 22) of heart 24 a time period $T_6$ after the detected atrial activation event $A_{ACT}$ 60J. In contrast, in some cases in which processing module 40 reverts LPD 10A back to the sensing without pacing mode, stimulation module 44 does not deliver ventricular pacing pulse $V_P$ 64E and heart 24 may skip a beat.

Figure 7:
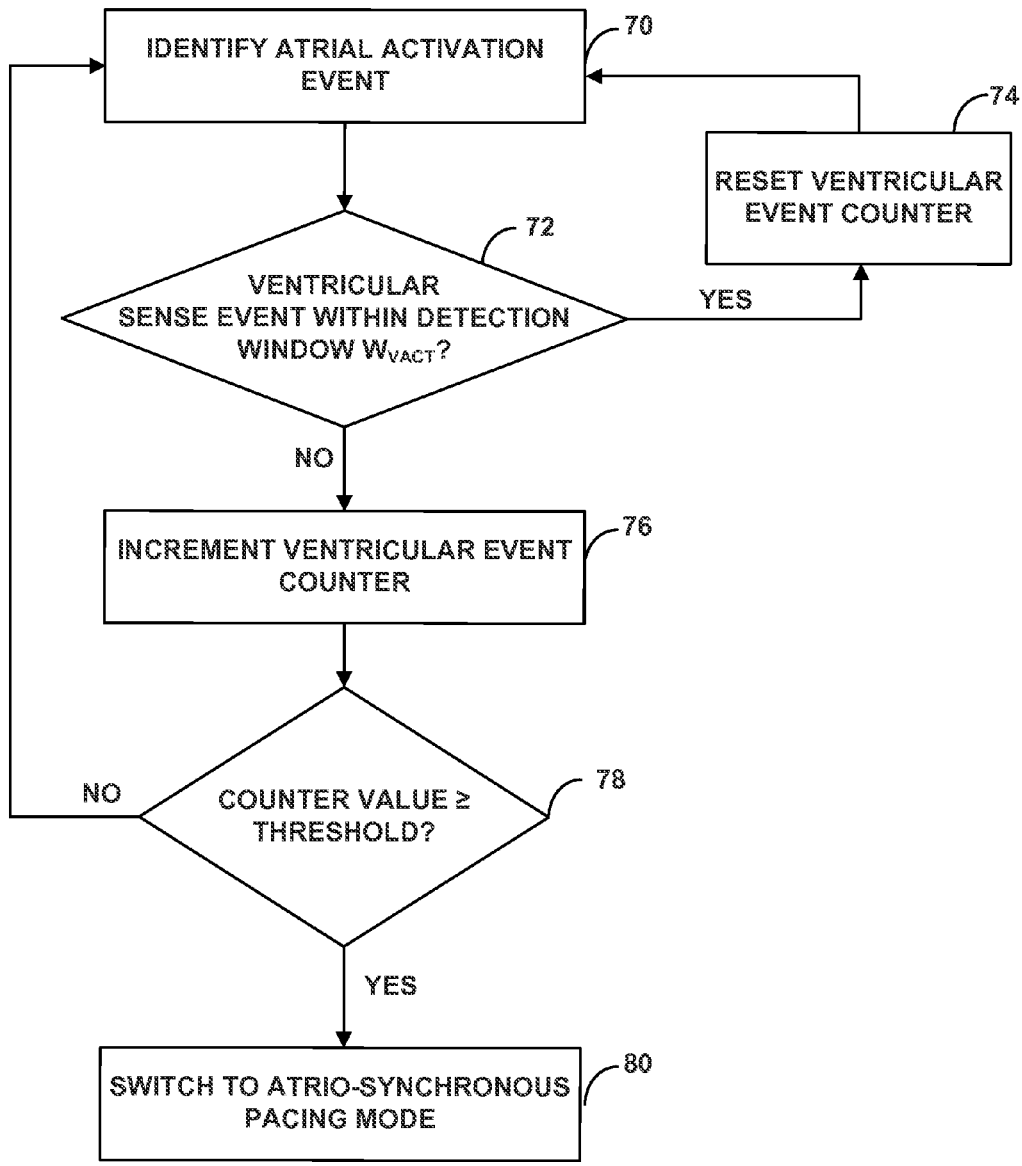
FIG. 7 is a flow diagram of an example technique for controlling a leadless pacing device implanted in a ventricle of a heart to switch from a sensing without pacing mode to an atrio-ventricular synchronous pacing mode.

FIG. 7 is a flow diagram of an example technique for operating LPD 10A. In the technique shown in FIG. 7, processing module 40 switches LPD 10A between a sensing without pacing mode and an atrio-ventricular synchronous pacing mode. While the technique shown in FIG. 7, as well as other techniques described herein, are primarily described as being performed by processing module 40, in other examples, the techniques described herein may be performed by another processing module (e.g., a processing module of another implanted device or an external device, such as a medical device programmer), alone or in combination with processing module 40. In addition, while right atrium 28 and right ventricle 22 are primarily referred to herein, in other examples, the devices, systems, and techniques described herein may also be used to control pacing therapy delivered to the left ventricle, to sense activity of the left atrium, or both.

In accordance with the technique shown in FIG. 7, processing module 40 identifies an atrial activation event $A_{ACT}$ while operating LPD 10A in a sensing without pacing mode (70). The atrial activation event may be, for example, an intrinsic or paced depolarization of right atrium 28, or a mechanical contraction of right atrium 28. Processing module 40 may determine, based on an electrical cardiac signal sensed by electrical sensing module 46, whether a ventricular sense event $V_S$ (e.g., an intrinsic ventricular depolarization) is detected within a ventricular event detection window $W_{V_{ACT}}$ that begins at the atrial activation event $A_{ACT}$ (72). In response to determining the ventricular sense event $V_S$ is detected within the ventricular event detection window $W_{V_{ACT}}$ ("YES" branch of block 72), processing module 40 may reset a ventricular event counter, and continue sensing cardiac activity in the sensing without pacing mode (70, 72).

The ventricular event counter may be used to count the number of cardiac cycles in which a ventricular depolarization $V_{ACT}$ was not detected within the ventricular event detection window $W_{V_{ACT}}$ that begins at a respective atrial activation event $A_{ACT}$. In the example shown in FIG. 7, the ventricular event counter may be used to count the number of cardiac cycles in which a ventricular depolarization $V_{ACT}$ was not detected within the ventricular event detection window $W_{V_{ACT}}$. The number of cardiac cycles may be consecutive or may be the number of cardiac cycles ("X") within a predetermined number of cardiac cycles ("Y"). In the latter example, the counter may be referred to as an "X of Y" style counter, where "X" indicates the number of cardiac cycles in which a ventricular depolarization $V_{ACT}$ was not detected and "Y" indicates a predetermined number of consecutive cardiac cycles.

In other examples, the ventricular event counter may be used to count the number of cardiac cycles within a predetermined period of time in which a ventricular depolarization $V_{ACT}$ was not detected within the ventricular event detection window $W_{V_{ACT}}$. Thus, in other examples of the technique shown in FIG. 7, processing module 40 may not reset the ventricular event counter (74) in response to detecting that, in one cardiac cycle, the ventricular sense event $V_S$ was detected within the ventricular event detection window $W_{V_{ACT}}$, but, rather, processing module 40 may reset the ventricular event counter at the end of a predetermined period of time.

In response to determining the ventricular sense event $V_S$ was not detected within the ventricular event detection window $W_{V_{ACT}}$ ("NO" branch of block 72), processing module 40 increments the ventricular event counter (76). The counter can be implemented by software, hardware, firmware, or any combination thereof. For example, when processing module 40 increments the counter, processing module 40 may generate a flag, value or other parameter or indication generated by processing module 40 and stored by memory 42 of LPD 10A or a memory of another device (e.g., another implanted device or an external medical device programmer). As another example, the counter may be implemented by a register-type circuit and processing module 40 may cause a state of the register-type circuit to change in order to increment or otherwise manage the counter. Counters having other configurations may also be used.

After incrementing the ventricular event counter (76), processing module 40 may determine whether the counter value is greater than or equal to a ventricular event threshold value (78). The ventricular event threshold value may indicate the number of cardiac cycles for which a ventricular event may not be detected within a ventricular event detection window $W_{V_{ACT}}$ or a shortened ventricular event detection window $W_{V_{ACT}}$ following an atrial activation event before LPD 10A delivers ventricular pacing therapy in an atrio-ventricular synchronous pacing mode. In some examples, such as the one shown in FIG. 6A, the ventricular event threshold value is one. In other examples, the ventricular event threshold value may be greater than one, such as two, three, or four or more.

The ventricular event threshold value may be value determined by a clinician to be indicative of a loss of intrinsic AV conduction, and may be selected to be low enough to configure LPD 10A to provide a responsive switch in operation mode, and to provide responsive cardiac rhythm management therapy. The ventricular event threshold value may be stored by memory 42 of LPD 10A or a memory of another device with which processing module 40 may communicate (e.g., a medical device programmer) via communication module 50 (FIG. 4).

In response to determining the counter value is less than the ventricular event threshold value ("NO" branch of block 78), processing module 40 may continue sensing cardiac activity in the sensing without pacing mode (70, 72). On the other hand, in response to determining the counter value is greater than or equal to the ventricular event threshold value ("YES" branch of block 78), processing module 40 may switch LPD 10A from the sensing without pacing mode to the atrio-ventricular synchronous pacing mode (80). An example of the atrio-ventricular synchronous pacing mode is described with reference to FIG. 8. A counter value greater than or equal to the ventricular event threshold value may indicate the presence of AV block.

In some examples, processing module 40 may reset the counter to zero each time a ventricular sense event $V_S$ is detected within the ventricular event detection window $W_{V_{ACT}}$. In other examples, processing module 40 increments the ventricular event counter for nonconsecutive cardiac cycles in which the ventricular depolarization is not detected within the ventricular event detection window $W_{V_{ACT}}$, and resets the counter at other times, e.g., if the ventricular depolarization is detected within the ventricular event detection window $W_{V_{ACT}}$ for two or more consecutive cardiac cycles. As another example, processing module 40 may manage the ventricular event counter to track the number of failures to detect the ventricular sense event $V_S$ within the ventricular event detection window $W_{V_{ACT}}$ for a predetermined range of time (e.g., within 30 seconds, one minute or more) or as an "X of Y" style counter. For example, processing module 40 may increment the ventricular event counter for each instance, for a predetermined time period, in which a ventricular depolarization is not detected within the ventricular event detection window $W_{V_{ACT}}$, and reset the counter at the end of the time range. As another example, processing module 40 may increment the ventricular event counter for each instance of a predetermined number of immediately prior cardiac cycles in which a ventricular depolarization is not detected within the ventricular event detection window $W_{V_{ACT}}$.

In some examples of the technique shown in FIG. 7, processing module 40 may generate a ventricular event indication in response to determining a ventricular sense event was not detected within the detection window $W_{V_{ACT}}$ and may increment the ventricular event counter by storing the ventricular event indication in memory 42 of LPD 10A or a memory of another device. Processing module 40 may reset the ventricular event counter by deleting the stored ventricular event indications. Processing module 40 may also determine whether the ventricular event counter value is greater than or equal to the threshold value (116) by at least determining whether the number of stored ventricular event indications is greater than or equal to the ventricular event threshold value.

The configuration of LPD 10A described with respect to FIGS. 6A, 6B, and 7, in which LPD 10A does not deliver ventricular pacing in the cardiac cycle in which a ventricular event was not detected by processing module 40, may permit electrical sensing module 46 to sense the intrinsic activity of heart 24 for at least one full beat before delivering a ventricular pacing pulse in an atrio-ventricular synchronous pacing mode. In this way, processing module 40 may take the time to sense the ventricular activation event, e.g., to permit heart 24 to resume intrinsic conduction, before LPD 10A delivers a ventricular pacing pulse, which may or may not correspond to the current heart rhythm of patient 26. By being configured to drop one or more heart beats, LPD 10A may be configured to promote the intrinsic conduction of heart 24 by giving LPD 10A the opportunity to sense intrinsic conduction of heart 24 before stimulation module 44 delivers ventricular pacing. This may help heart 24 stay synchronized.

Figure 8:
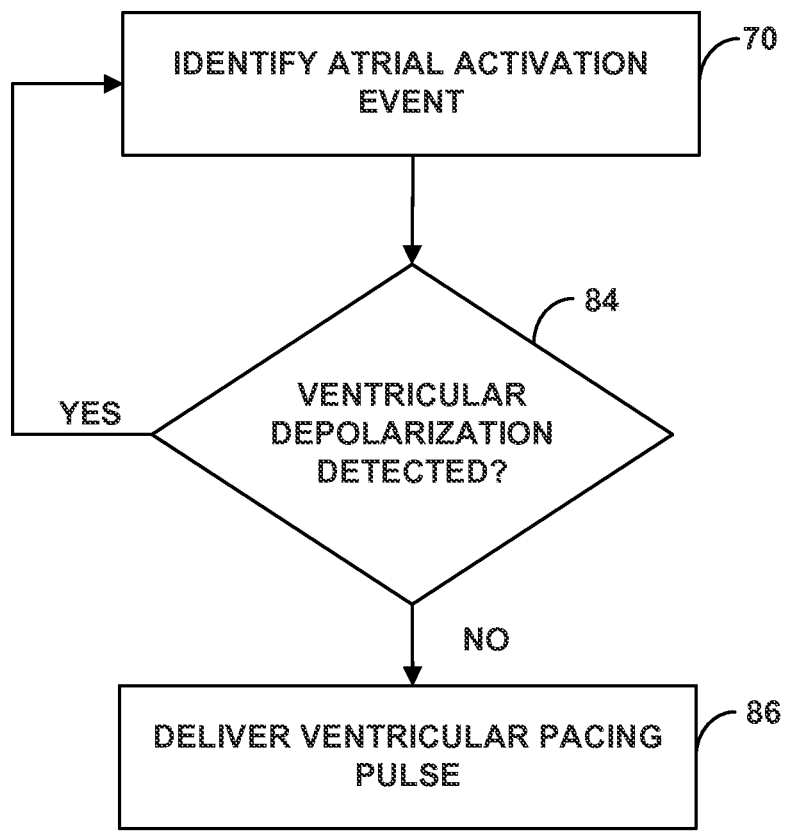
FIG. 8 is a flow diagram of an example technique for delivering pacing pulses to a ventricle of a heart in accordance with an atrio-ventricular synchronous pacing mode.

FIG. 8 is a flow diagram of an example technique for delivering pacing pulses to a ventricle of heart 24 in accordance with an atrio-ventricular synchronous pacing mode. Processing module 40 identifies an atrial activation event (70), determines whether an intrinsic ventricular sense event $V_S$ (e.g., an R-wave) is detected subsequent to the atrial activation event, e.g., within an AV interval beginning when the atrial activation event was detected or within a ventricular event detection window $W_{VACT}$.

In response to determining the ventricular sense event was not detected subsequent to the atrial activation event ("NO" branch of block 84), processing module 40 may control stimulation module 44 to generate and deliver a pacing pulse to right ventricle 22 of heart 24 (88). In response to determining the ventricular sense event was detected subsequent to the atrial activation event ("YES" branch of block 84), LPD 10A may not deliver a ventricular pacing pulse, but, rather, processing module 40 may continue to monitor the cardiac activity of patient 26 (70, 84). For patients with intermittent AV node conduction, it may be preferable to inhibit ventricular pacing by LPD 10A in accordance with the technique shown in FIG. 8 and allow an intrinsic ventricular depolarization to occur for a time, e.g., the AV interval, after an intrinsic atrial depolarization or atrial pace.

In some examples, LPD 10A may undersense atrial activity (e.g., intrinsic depolarizations or atrial pacing activity) of heart 24, which may affect the delivery of ventricular pacing pulses when LPD 10A is operating in the atrio-ventricular synchronous pacing mode (e.g., as shown in FIG. 8). In accordance with some examples described herein, LPD 10A is configured to automatically switch (without user intervention in some cases) from the atrio-ventricular synchronous pacing mode to an asynchronous ventricular pacing mode in response to detecting an atrial undersense event.

Figure 9:
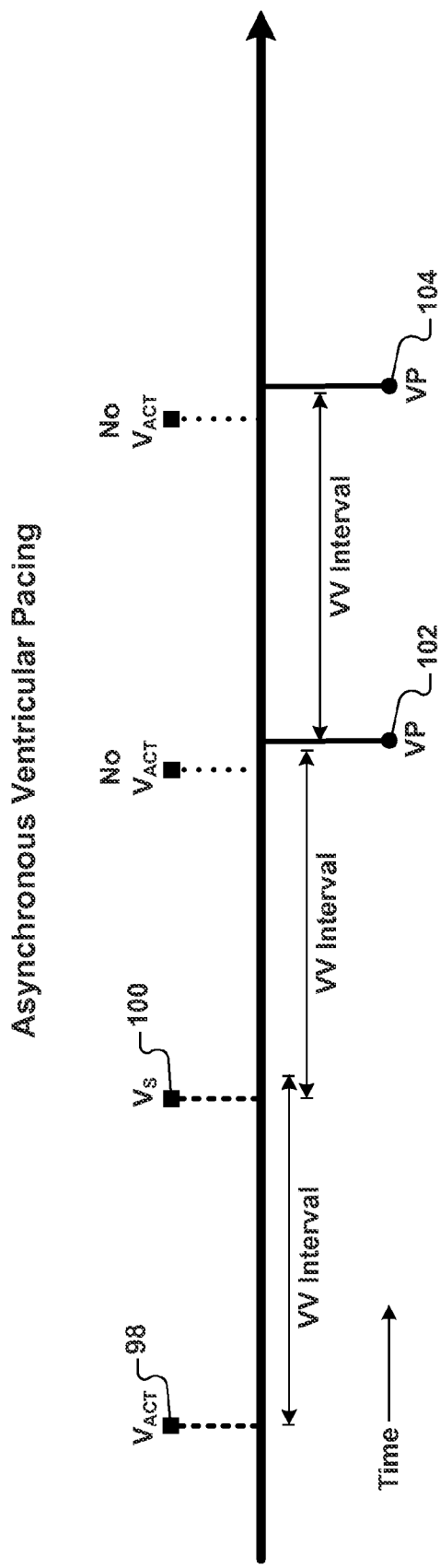
FIG. 9 is a timing diagram illustrating an example of asynchronous ventricular pacing.

FIG. 9 is a timing diagram illustrating an example of asynchronous ventricular pacing and is described with reference to FIG. 10, which is a flow diagram of an example technique for delivering asynchronous ventricular pacing. In the technique shown in FIG. 10, processing module 40 identifies a ventricular activation event $V_{ACT}$ (90), which may be a delivery of a ventricular pacing pulse or an intrinsic depolarization of right ventricle 22 (e.g., an R-wave in an electrical cardiac signal sensed by sensing module 46). Processing module 40 determines whether an intrinsic depolarization of right ventricle 22 is detected within a within a VV interval that begins when the ventricular activation was detected (e.g., when the previous intrinsic ventricular depolarization was detected, or a previous ventricular pacing pulse was delivered) (92).

The VV interval may have any suitable length. In some examples, processing module 40 determines the VV interval based on sensed cardiac activity of patient 26 and stores in the interval in memory 42. For example, processing module 40 may determine the VV interval to be the average or median time between consecutive ventricular activation events (e.g., consecutive intrinsic ventricular depolarizations detected by electrical sensing module 44) for a certain number of cardiac cycles immediately preceding the present cardiac cycle. The certain number can be, for example, two or more, such as six, ten, twelve, twenty, or thirty. In some examples, processing module times the delivery of ventricular pacing pulses delivered in the asynchronous ventricular pacing mode using the VV interval. In this case, the VV interval may be slightly longer than the heart rate of patient 26, which may be determined from data from a sensor.

In other examples, processing module 40 may use a preprogrammed VV interval. This, however, may be lower than the patient's current heart rate, which may cause a relatively abrupt change in the heart rate of patient 26, which may not be desired. Controlling the timing of ventricular pacing pulse $V_P$ delivered in accordance with the asynchronous ventricular pacing mode based on the VV interval determined based on sensed cardiac activity of patient 26 may help smooth the heart rate of patient 26, particularly when compared controlling the timing of the pacing pulses based on a preprogrammed rate.

In some examples, processing module 40 determines the VV interval to be the greater of the VV interval determined based on sensed cardiac activity of patient 26 or a preprogrammed rate. This may enable processing module 40 to provide some minimum pacing rate, which may further help smooth the heart rate of patient 26.

In any of the examples described above, processing module 40 may also modify the VV interval based on detected changes in the heart rate of patient 26. For example, processing module 40 may increase the VV interval as heart rate decreases, and decrease the VV interval as the heart rate increases. In this way, processing module 40 may provide rate adaptive asynchronous ventricular pacing.

In response to determining the intrinsic depolarization of right ventricle 22 was detected within the VV interval ("YES" branch of block 92), processing module 40 may determine the sensed intrinsic depolarization of right ventricle 22 was a ventricular activation (90) and determine whether a subsequent intrinsic depolarization of right ventricle 22 is detected within a within a VV interval (92). For example, in the timing diagram shown in FIG. 9, after processing module 40 identifies ventricular activation event $V_{ACT}$ 98, processing module 40 may determine, based on a sensed electrical cardiac signal, that an intrinsic depolarization of right ventricle 22 $V_S$ 100 is detected within a VV interval that begins at ventricular activation event $V_{ACT}$ 98. Processing module 40 may then determine whether a intrinsic depolarization of right ventricle 22 is detected within the VV interval that begins at intrinsic depolarization of right ventricle 22 $V_S$ 100 (92)

In response to determining the intrinsic depolarization of right ventricle 22 was not detected within the VV interval ("NO" branch of block 92), processing module 40 may control stimulation module 44 to deliver a ventricular pacing pulse to right ventricle 22 (94). For example, in the timing diagram shown in FIG. 9, after processing module 40 determines, based on a sensed electrical cardiac signal, that an intrinsic depolarization of right ventricle 22 $V_S$ was not detected within a VV interval that begins at ventricular sense event $V_s$ 100, processing module 40 may control stimulation module 44 to deliver a ventricular pacing pulse $V_P$ 102 to right ventricle 22. The ventricular pacing pulse may be delivered at the end of the VV interval that begins at the prior detected ventricular activation event $V_S$ 100.

Processing module 40 may then identify ventricular pacing pulse $V_P$ 102 as a ventricular activation event (90) and determine whether an intrinsic depolarization of right ventricle 22 is detected within a within a VV interval that begins at ventricular pacing pulse $V_P$ 102 (92). In the example timing diagram shown in FIG. 9, processing module 40 determines, based on a sensed electrical cardiac signal, that an intrinsic depolarization of right ventricle 22 $V_S$ was not detected within a VV interval that begins at ventricular pacing pulse $V_P$ 102. Thus, processing module 40 may control stimulation module 44 to deliver a ventricular pacing pulse $V_P$ 104 to right ventricle 22.

Figure 11:
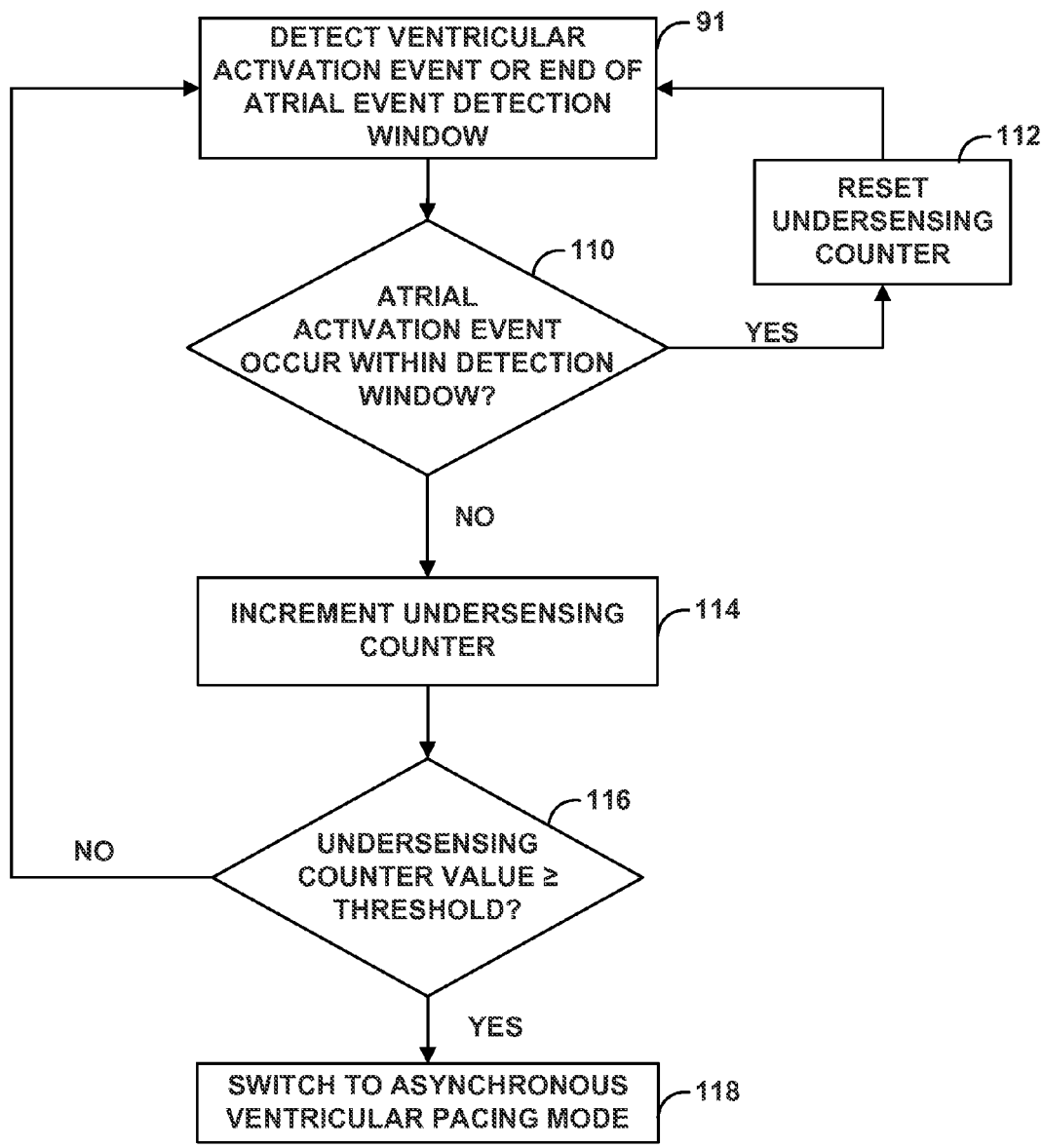
FIG. 11 is a flow diagram of an example technique for controlling a leadless pacing device implanted in a ventricle of a heart to switch from an atrio-ventricular synchronous pacing mode to asynchronous ventricular pacing mode.

FIG. 11 is a flow diagram of an example technique for switching LPD 10A (or another LPD) from an atrio-ventricular synchronous pacing mode to asynchronous ventricular pacing mode in response to detecting an atrial undersensing event. When the switch is performed, processing module 40 controls stimulation module 44 to stop delivering pacing pulses to right ventricle 22 in the atrio-ventricular synchronous pacing mode, in which ventricular pacing pulses are timed to an atrial activation event, and controls stimulation module 44 to deliver pacing pulses to right ventricle 22 in the asynchronous ventricular pacing mode, in which ventricular pacing pulses are timed relative to a ventricular activation event.

In accordance with the technique shown in FIG. 11, while processing module 40 is controlling stimulation module 44 to deliver ventricular pacing pulses to right ventricle 22 of heart 24 of patient 26 according to an atrio-ventricular synchronous pacing mode, processing module 40 may detect a ventricular activation event $V_{ACT}$ (91), and determine whether an atrial activation event $A_{ACT}$ is detected within an atrial event detection window $W_{AACT}$ that begins at the prior atrial activation event $A_{ACT}$ (110). In other examples, the atrial event detection window $W_{AACT}$ may begin at the prior ventricular activation event, which can be can be, for example, the delivery of a ventricular pacing pulse ($V_P$) or an intrinsic ventricular depolarization ($V_S$) (e.g., an R-wave detected within a sensed electrical cardiac signal). In some examples, LPD 10A may be configured to detect contraction of right ventricle 22 based on the motion signal, and identify activation of the ventricle based on the detected ventricular contraction. Similarly, the atrial activation event can be, for example, an intrinsic atrial depolarization, an atrial paced event, or a mechanical contraction of the atrium sensed by LPD 10A.

The atrial event detection window $W_{AACT}$ may define a listening period during which processing module 40 analyzes a sensed electrical cardiac signal (or another physiological signal) to detect an atrial activation event. In some examples, the duration of the atrial event detection window $W_{AACT}$ is based on the average or median A-A interval for a predetermined number of past cardiac cycles, such as the past six to 12 cardiac cycles. In some examples, the atrial event detection window $W_{AACT}$ is between about 350 ms and about 1200 ms patients. In yet other examples, the duration of the atrial event detection window $W_{AACT}$ is based on the average or median VV interval for a predetermined number of past cardiac cycles, such as the past six to 12 cardiac cycles.

In response to detecting an atrial activation event $A_{ACT}$ within an atrial event detection window $W_{AACT}$ ("YES" branch of block 110), processing module 40 may reset a counter that is used to track the number of cardiac cycles in which an atrial activation event $A_{ACT}$ is not detected within a respective atrial event detection window $W_{AACT}$ (112), referred to herein as an undersensing counter. In some examples, the undersensing counter may count a number of undersensing indications and may be configured in the same way as the ventricular event counter (described with respect to FIG. 7). In some examples, the undersensing counter may be used to count the number of consecutive cardiac cycles in which an atrial activation event $A_{ACT}$ is not detected within a respective atrial event detection window $W_{AACT}$, and processing module 40 may reset the counter by returning the counter to zero in some examples. In other examples, the undersensing counter may be used to count the number of cardiac cycles within a predetermined period of time or a predetermined number of cardiac cycles in which an atrial activation event $A_{ACT}$ is not detected within a respective atrial event detection window $W_{AACT}$. In some examples in which an "X of Y" type counter is used, processing module 40 may reset the counter by removing any counts included in the "X" value that correspond to undersensing indications that occurred prior to the "Y" number of preceding cardiac cycles. In other examples of the technique shown in FIG. 11, processing module 40 may not reset the undersensing counter (112) in response to detecting that, in one cardiac cycle, the atrial activation event $A_{ACT}$ is detected within the atrial event detection window, but, rather, processing module 40 may reset the undersensing counter at the end of a predetermined period of time.

Processing module 40 may identify a next ventricular activation event or the end of the next atrial activation event detection window (91) and repeat the technique shown in FIG. 11. In response to determining that an atrial activation event $A_{ACT}$ is not detected within the next atrial event detection window $W_{AACT}$ ("NO" branch of block 110), processing module 40 generates an undersensing indication and increments the undersensing counter (114). In some cases, the atrial activation event may occur, but may be detected by processing module 40 outside of the atrial event detection window $W_{AACT}$, after the end of the atrial event detection window. In other cases, the atrial activation event may not occur or may not be detected by processing module 40 prior to a next ventricular activation event is detected. In either case, the lack of detection of the atrial activation event may be determined to be not within an atrial event detection window $W_{AACT}$ and the result of atrial undersensing by LPD 10A.

Processing module 40 determines whether the undersensing counter value is greater than or equal to an undersensing threshold value (116). The undersensing threshold value may indicate the number of cardiac cycles for which an atrial activation event may not be detected within an atrial activation event detection window $W_{AACT}$ that begins at an immediately prior detected atrial activation event $A_{ACT}$ before processing module 40 detects an atrial undersensing event and controls LPD 10A to switch to the asynchronous ventricular pacing mode. The undersensing threshold value may be stored by memory 42 of LPD 10A or a memory of another device with which processing module 40 may communicate (e.g., a medical device programmer).

In some examples, the undersensing threshold value is one. In other examples, the undersensing threshold value may be greater than one, such as two, three, or four or more. The undersensing threshold value may be selected to be low enough to configure LPD 10A to responsively switch operation mode to provide responsive cardiac rhythm management therapy, yet high enough to provide LPD 10A with time to determine whether an atrial activation event will be eventually be sensed by LPD 10A within a time period in which LPD 10A may still deliver effective atrio-ventricular synchronous pacing. This may permit heart 24 to maintain intrinsic conduction because if sensing module 40 of LPD 10A senses an atrial activation event, then LPD 10A may continue delivering atrio-ventricular synchronous pacing, which favors synchrony of right ventricle 22 with right atrium 28.

In the atrio-ventricular synchronous pacing mode, processing module 40 controls stimulation module 44 to generate and deliver a ventricular pacing pulse to right ventricle 22 (or the left ventricle in other examples) a predetermined time period $T_6$ after a detected atrial activation event $A_{ACT}$. In this way, the atrial activation event $A_{ACT}$ may be used to time the delivery of a ventricular pacing pulse in the atrio-ventricular synchronous pacing mode. In some examples, the time period $T_6$ is based on stored VV interval data. For example time period $T_6$ may be selected such that the VV interval for that cardiac cycle is substantially equal (e.g., equal or nearly equal) to average or median VV interval for a certain number of immediately preceding cardiac cycles.

Figure 12:
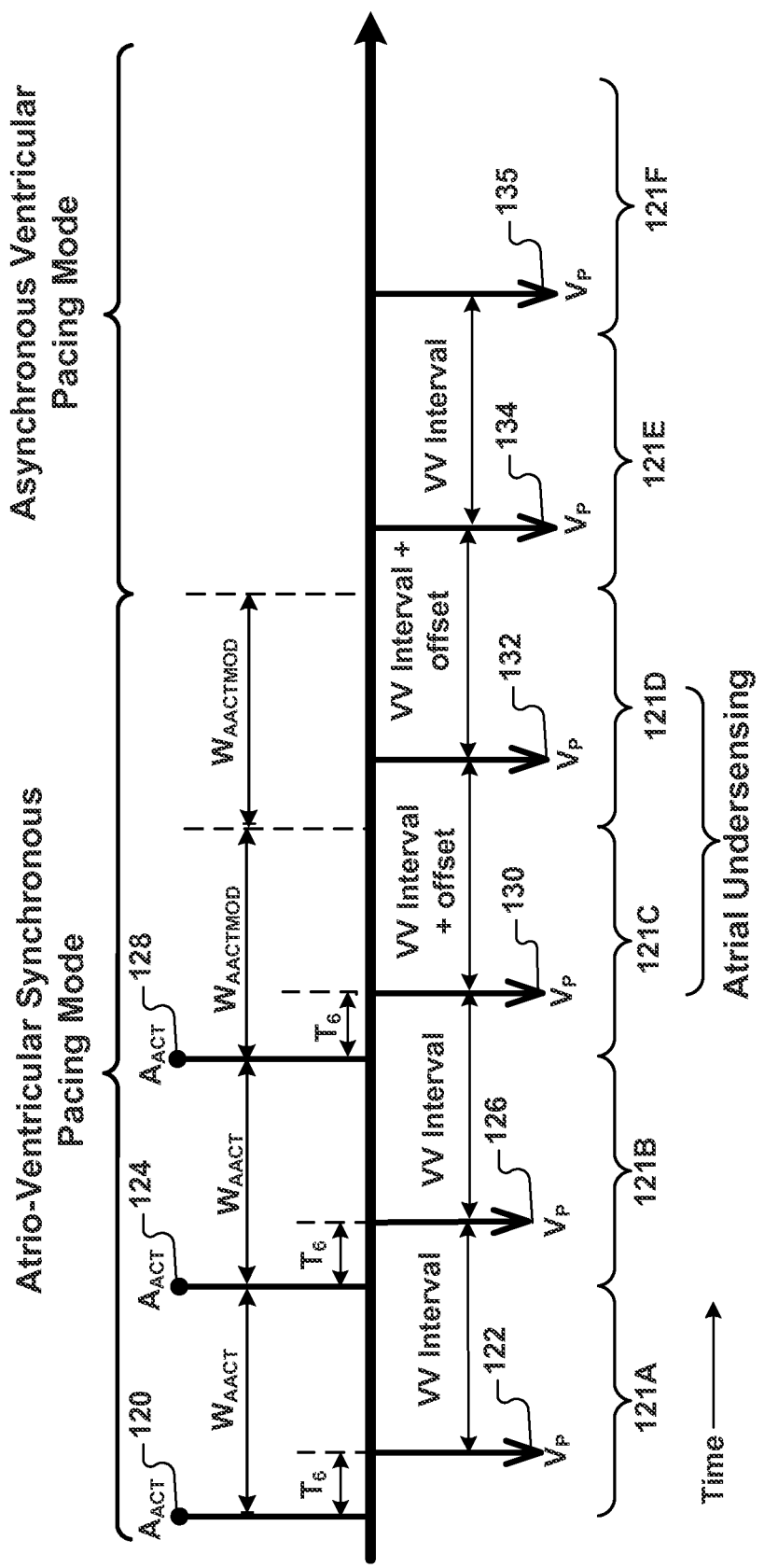
FIG. 12 is a timing diagram illustrating example application of the technique of FIG. 11.

In cardiac cycles in which processing module 40 does not detect an atrial activation event $A_{ACT}$ within an atrial event detection window $W_{AACT}$ ("NO" branch of block 110), processing module 40 may control the timing of a ventricular pacing pulse by stimulation module 44 based on the prior ventricular pacing pulse. As shown in FIG. 12, for example, processing module 40 may control stimulation module 44 to deliver a ventricular pacing pulse a time period after the prior ventricular pacing pulse (or other ventricular activation event), the time period being substantially equal to the "VV interval+offset." The "VV interval+offset" may be substantially equal to average or median VV interval for a certain number of immediately preceding cardiac cycles plus an offset, which adds time to the VV interval. As a result, the pacing pulse may be delivered after time period $T_6$, but still in a timely manner. In some cases, the additional amount of time is about 50 milliseconds to about 250 milliseconds, such as about 100 milliseconds, or a percentage of the VV intervals By timing the delivery of a ventricular pacing pulse based on a detected atrial activation event in the atrio-ventricular synchronous mode, processing module 40 may time the ventricular pacing pulse based on the current heart rate of patient 26.

If the undersensing counter value is not greater than or equal to an undersensing threshold value, then processing module 40 may determine that no atrial undersensing event was detected. Thus, in response to determining the undersensing counter value is less than the undersensing threshold value ("NO" branch of block 116), processing module 40 may continue to monitor the cardiac activity of patient 26 using the technique shown in FIG. 11 until an atrial undersensing event is detected. In some examples, however, processing module 40 may not detect a ventricular activation event (91), if, for example, stimulation module 44 did not deliver a ventricular pacing pulse in the cardiac cycle in which the atrial activation event was not detected. Thus, rather than detecting a ventricular activation event, processing module 40 may identify the end of the prior atrial event detection window $W_{AACT}$ (91) and determine whether an atrial activation event is detected within a modified atrial event detection window $W_{AACTMOD}$ that begins at the end of the atrial event detection window $W_{AACT}$. The modified atrial event detection window $W_{AACTMOD}$ may have a longer duration than the atrial event detection window $W_{AACT}$ in some examples.

In some examples, the atrial event detection window $W_{AACT}$ has a duration that is based on the VV interval of prior detected ventricular activation events. For example, the atrial event detection window may be the longest, shortest, or average duration of the last two, three, four or more (e.g., ten or more) VV intervals for those cardiac cycles in which processing module 40 detected atrial activation events, plus an additional amount of time.

The modified atrial event detection window $W_{AACTMOD}$ may be the atrial event detection window $W_{AACT}$ plus an additional amount of time to account for a change in the heart rate of patient 26. The offset may be from about 30 ms to about 100 ms, such as about 50 ms or about 100 ms, or may be in a range from about 50 ms to about 150 ms. In other examples, the offset may be from about 50 ms to about 150 ms, which may be in the 10 to 20 beats per minute heart rate range.

Processing module 40 may store the atrial event detection window $W_{AACT}$, the modified atrial event detection window $W_{AACTMOD}$, the A-A intervals for the latest detected atrial activation events, the offset, or any combination thereof, in memory 42 of LPD 10A or a memory of another device.

Processing module 40 may detect an atrial undersensing event in response to determining the undersensing counter value is greater than or equal to an undersensing threshold value ("YES" branch of block 116). As shown in FIG. 11, in response to determining the undersensing counter value is greater than or equal to an undersensing threshold value ("YES" branch of block 116), processing module 40 may switch LPD 10A from the atrio-ventricular synchronous pacing mode to an asynchronous ventricular pacing mode (118). Thus, processing module 40 may control the delivery of ventricular pacing pulses to right ventricle 22 of heart 24 of patient 26 using an asynchronous ventricular pacing mode, e.g., such as that shown and described with respect to FIGS. 9 and 10.

In some examples, processing module 40 generates an indication of the undersensing event and stores the indication in memory 42 or a memory of another device. The indication may be, for example, a flag, value, or other parameter. The number and timing of the undersensing events may be used by a clinician at a later time to evaluate the patient condition or the therapy.

In some examples of the technique shown in FIG. 11, processing module 40 may generate an undersensing indication in response to determining an atrial activation event $A_{ACT}$ is not detected within a respective atrial event detection window $W_{AACT}$ and may increment the undersensing counter by storing the undersensing indication in memory 42 of LPD 10A or a memory of another device. Processing module 40 may reset the undersensing counter by, for example, deleting the stored undersensing indications, or by deleting the stored undersensing indications that occurred prior to the "Y" number of preceding cardiac cycles when an "X of Y" type counter is used. Processing module 40 may also determine whether the undersensing counter value is greater than or equal to the threshold value (116) by at least determining whether the number of stored undersensing indications is greater than or equal to the undersensing threshold value.

FIG. 12 is a timing diagram illustrating example application of the technique of FIG. 11 for switching from an atrio-ventricular synchronous pacing mode to an asynchronous ventricular pacing mode in response to detecting an undersensing event. The example shown in FIG. 12, the ventricular activation events are shown as ventricular pacing pulses $V_P$, but at least some of the ventricular activation events may be intrinsic ventricular depolarizations in other examples.

As shown in FIG. 12, processing module 40 may control the delivery of ventricular pacing pulses to right ventricle 22 in an atrio-ventricular synchronous pacing mode. For example, as described with respect to FIG. 7, processing module 40 may detect an atrial activation event $A_{ACT}$ 120 based on an electrical cardiac signal sensed by electrical sensing module 46, based on the detection of the delivery of an atrial pacing pulse, or using another technique. Processing module 40 may determine, e.g., using the technique shown in FIG. 8, whether an intrinsic ventricular depolarization is detected within a ventricular sense event detection window $W_{VACT}$ or $W_{ACTSHORT}$ (not labeled in FIG. 12). In the example shown in FIG. 12, in cardiac cycle 121A, processing module 40 determines that an intrinsic ventricular depolarization was not detected within the ventricular sense event detection window and controls stimulation module 44 to deliver a ventricular pacing pulse $V_P$ 122 to right ventricle 22 a time period $T_6$ after the detected atrial activation event $A_{ACT}$ 120.

In a next cardiac cycle 121B (immediately after cardiac cycle 121A), processing module 40 determines that an atrial activation event $A_{ACT}$ 124 is detected within an atrial event detection window $W_{AACT}$ that begins at the atrial activation event 120 (110). In accordance with the technique shown in FIG. 11, processing module 40 may then reset the undersensing counter (112) and control stimulation module 44 to deliver ventricular pacing pulse $V_P$ 126 to right ventricle 22 a time period $T_6$ after the detected atrial activation event $A_{ACT}$ 124. Similarly, in the following cardiac cycle 121C, processing module 40 determines that an atrial activation event $A_{ACT}$ 128 is detected within an atrial event detection window $W_{AACT}$ of the prior cardiac cycle 121B (110). Processing module 40 may then reset the undersensing counter (112) and control stimulation module 44 to deliver ventricular pacing pulse $V_P$ 130 to right ventricle 22 a time period $T_6$ after a detected atrial activation event $A_{ACT}$ 128.

In the following cardiac cycle 121D, processing module 40 determines that an atrial activation event $A_{ACT}$ was not detected within a modified atrial event detection window $W_{AACTMOD}$ that begins at the atrial activation event $A_{ACT}$ 128 ("NO" branch of block 110 in FIG. 11). The longer atrial event detection window may be used in this instance in order to provide processing module 40 with an atrial activation event listening period that is sufficiently long. For example, in some examples, the longer atrial event detection window may be greater than the average A-A interval for a predetermined number (e.g., 5, 10, or more) of the immediately preceding cardiac cycles. As another example, the longer atrial event detection window may have a predetermined, preprogrammed duration.

In response to determining an atrial activation event $A_{ACT}$ was not detected within a modified atrial event detection window $W_{AACTMOD}$, processing module 40 may increment the undersensing counter (114) and determine whether the undersensing counter value is greater than or equal to the undersensing threshold value (116). In the example shown in FIG. 12, processing module 40 determines in cardiac cycle 121D that the undersensing counter value is not greater than or equal to the undersensing threshold value ("NO" branch of block 116). Thus, processing module 40 may control stimulation module 44 to deliver a ventricular pacing pulse $V_P$ 132 to right ventricle 22, which is timed to ventricular pacing pulse 130 of the immediately preceding cardiac cycle 121C. In the example shown in FIG. 12, stimulation module 44 delivers ventricular pacing pulse $V_P$ 132 a time period after ventricular pacing pulse 130, where the time period is substantially equal to (e.g., equal to or nearly equal to) a VV interval plus an offset (VV interval+offset"). The offset may be 30 ms to about 100 ms, such as about 50 ms or about 100 ms. This way, the VV intervals only slightly extend due to the atrial undersense.

In the following cardiac cycle 121E, however, processing module 40 determines that an atrial activation event $A_{ACT}$ was not detected within a modified atrial event detection window $W_{AACTMOD}$ that began at the end of the atrial activation event window of the prior cardiac cycle 121D ("NO" branch of block 110 in FIG. 11). Processing module 40 may control stimulation module 44 to deliver a ventricular pacing pulse $V_P$ 134 to right ventricle 22, which is timed to ventricular pacing pulse 130 of the immediately preceding cardiac cycle 121D.

In addition, in response to determining that an atrial activation event $A_{ACT}$ was not detected within a modified atrial event detection window $W_{AACTMOD}$ that began at the end of the atrial activation event window of the prior cardiac cycle 121D, processing module 40 may increment the undersensing counter (114) and determine whether the undersensing counter value is greater than or equal to the undersensing threshold value (116). In the example shown in FIG. 12, processing module 40 determines in cardiac cycle 121E that the undersensing counter value is greater than or equal to the undersensing threshold value ("YES" branch of block 116). Thus, processing module 40 determines that an undersensing event is detected and switches LPD 10A to the asynchronous ventricular pacing mode. In the example shown in FIG. 12, in the first cardiac cycle 121F LPD 10A is in the asynchronous pacing mode, stimulation module 44 delivers a ventricular pacing pulse $V_P$ 135 to heart 24 a VV interval after pacing pulse 134 of the prior cardiac cycle 121E.

Figure 10:
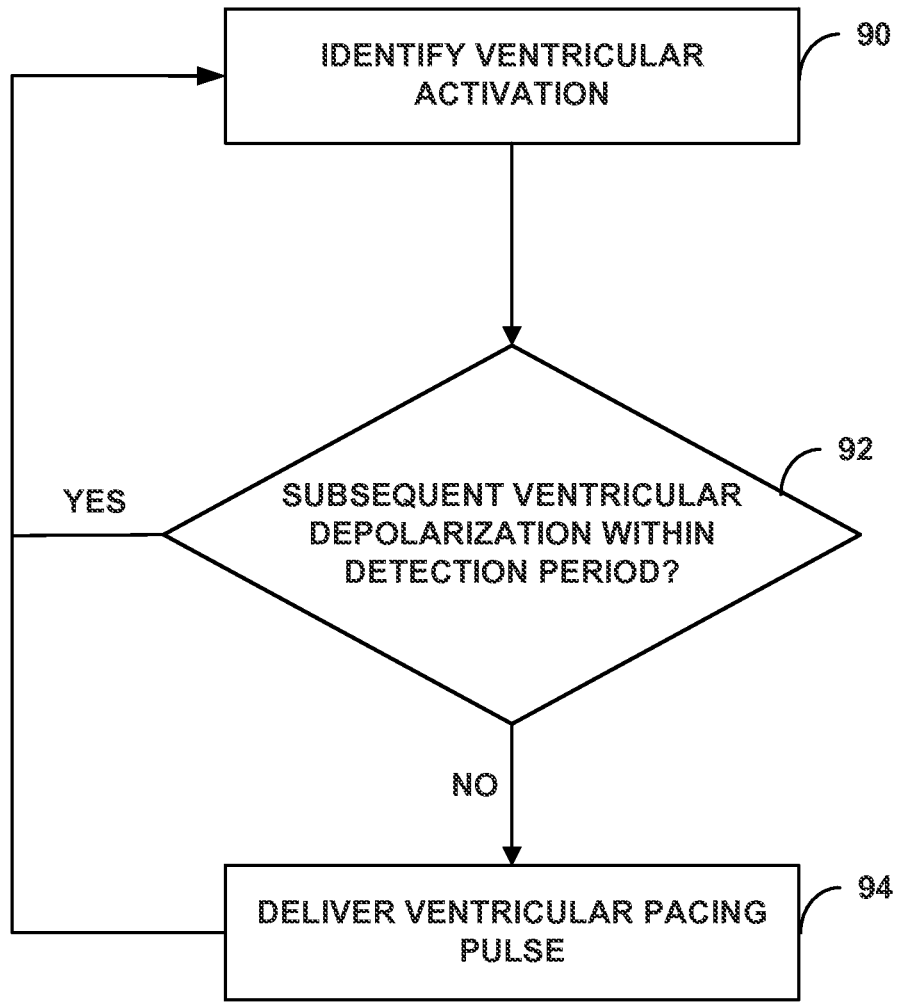
FIG. 10 is a flow diagram of an example technique for delivering pacing pulses to a ventricle of a heart in accordance with an asynchronous ventricular pacing mode.

As described with respect to FIGS. 9 and 10, in the asynchronous ventricular pacing mode, processing module 40 may determine whether an intrinsic depolarization of right ventricle 22 is detected within a within a VV interval that begins when a ventricular activation was detected (e.g., VP 132), and in response to determining the intrinsic depolarization of right ventricle 22 was not detected within the VV interval, processing module 40 may control stimulation module 44 to deliver a ventricular pacing pulse $V_P$ 134 to right ventricle 22. In the example shown in FIG. 12, the time period between subsequent pacing pulses 132, 134 is shown as the VV interval of one or more prior cardiac cycles, plus an offset (e.g., about 30 ms to about 150 ms, such as about 50 ms or about 100 ms, though it may vary based on the heart rate). In some examples, processing module 40 determines the VV interval based on one or more prior cardiac cycles, such as cardiac cycles 121A, 121B. For example, the VV interval may be the average interval between ventricular activation events of the one or more prior cardiac cycles. The VV interval may indicate the average or median heart rate, such that the offset results in a pacing rate that may be lower than the prior detected heart rate of patient 26.

On the other hand, if processing module 40 determined the intrinsic depolarization of right ventricle 22 was detected within the VV interval, then processing module 40 may not control stimulation module 44 to deliver a ventricular pacing pulse $V_P$ 134 to right ventricle 22.

LPD 10A may intermittently sense atrial activation events, even when in the asynchronous pacing mode. In some situations, it may be desirable for LPD 10A to deliver atrio-ventricular synchronous pacing when possible in order to help heart 26 maintain synchrony. Thus, in some examples described herein, after processing module 40 controls LPD 10A to switch from an atrio-ventricular synchronous pacing mode to an asynchronous ventricular pacing mode, processing module 40 may periodically determine whether an atrial activation event is detected. In response to determining an atrial activation is detected, processing module 40 may control LPD 10A to revert back to the atrio-ventricular synchronous pacing mode. An LPD 10A configured in this manner may deliver rate responsive pacing when the atrial rate is too slow or consistent atrial undersensing is occurring, while favoring AV synchronous pacing over asynchronous pacing.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
sensing an electrical cardiac signal of a patient with a leadless pacing device while the leadless pacing device is in a sensing without pacing mode;
receiving, by a processing module, the electrical cardiac signal;
detecting, by the processing module and based on the electrical cardiac signal, an atrial activation event;
determining, by the processing module and based on the electrical cardiac signal, a ventricular sense event was not detected within a ventricular event detection window that begins at the atrial activation event; and
controlling, by the processing module, the leadless pacing device to switch from the sensing without pacing mode to an atrio-ventricular synchronous pacing mode based on the determination that the ventricular sense event was not detected within the ventricular event detection window, wherein controlling the leadless pacing device to switch to the atrio-ventricular synchronous pacing mode comprises controlling the leadless pacing device to deliver a pacing pulse to the patient according to the atrio-ventricular synchronous pacing mode after detecting an additional atrial activation event.

2. The method of claim 1, comprising sensing of a first cardiac cycle and a second cardiac cycle immediately following the first cardiac cycle, wherein controlling the leadless pacing device to deliver the pacing pulse to the patient according to the atrio-ventricular synchronous pacing mode comprises controlling the leadless pacing device to deliver the pacing pulse to the patient according to the atrio-ventricular synchronous pacing mode in the first cardiac cycle, the method further comprising, in the second cardiac cycle, controlling, by the processing module, the leadless pacing device to switch from the atrio-ventricular synchronous pacing mode to the sensing without pacing mode.

3. The method of claim 2, wherein the electrical cardiac signal comprises a first electrical cardiac signal and the atrial activation event comprises a first atrial activation event, the method further comprising, after controlling the leadless pacing device to switch from the atrio-ventricular synchronous pacing mode to the sensing without pacing mode:
receiving, by the processing module, a second electrical cardiac signal of the patient sensed by the leadless pacing device after the first cardiac cycle and while the leadless pacing device is in the sensing without pacing mode;
detecting, by the processing module and based on the second electrical cardiac signal, a second atrial activation event;
determining, by the processing module and based on the second electrical cardiac signal, the ventricular sense event was not detected within the ventricular event detection window that begins at the second atrial activation event; and
controlling, by the processing module, the leadless pacing device to switch from the sensing without pacing mode to the atrio-ventricular synchronous pacing mode based on the determination that the ventricular sense event was not detected within the ventricular event detection window that begins at the second atrial activation event.

4. The method of claim 1, wherein controlling the leadless pacing device to switch from the sensing without pacing mode to the atrio-ventricular synchronous pacing mode further comprises:
in response to determining the ventricular sense event was not detected within the detection window, incrementing a counter;
after incrementing the counter, determining, by the processing module, whether a value of the counter is greater than or equal to a threshold value; and in response to determining the value of the counter is greater than or equal to a threshold value, controlling, by the processing module, the leadless pacing device to deliver the pacing pulse according to the atrio-ventricular synchronous pacing.

5. The method of claim 4, wherein the threshold value is one.

6. The method of claim 4, wherein the threshold value is two or three.

7. The method of claim 1, wherein detecting the atrial activation event comprises detecting a P wave in the sensed electrical cardiac signal.

8. The method of claim 1, wherein detecting the atrial activation event comprises detecting delivery of an atrial pacing pulse by a medical device different than the leadless pacing device.

9. The method of claim 1, further comprising storing A-A intervals for a predetermined number of prior cardiac cycles of the patient and determining the ventricular event detection window based on the stored A-A intervals.

10. The method of claim 9, wherein determining the ventricular event detection window comprises determining at least one of: a mean A-A interval of the stored A-A intervals, a median A-A interval of the stored A-A intervals, a greatest A-A interval of the stored A-A intervals, a shortest A-A interval of the stored A-A intervals, or a most recent A-A interval of the stored A-A intervals.

11. The method of claim 10, wherein determining the ventricular event detection window comprises determining a predetermined percentage of the at least one of the mean A-A interval, the median A-A interval, the greatest A-A interval, the shortest A-A interval, or the most recent A-A interval.

12. The method of claim 9, wherein determining the ventricular event detection window comprises selecting the smaller of a first ventricular event detection window determined based on the stored A-A intervals for a predetermined number of prior cardiac cycles or a second, fixed ventricular event detection window stored by the leadless pacing device.

13. The method of claim 1, further comprising receiving, by the processing module, data indicating a duration of the ventricular event detection window from a medical device programmer.

14. The method of claim 1, further comprising, after controlling the leadless pacing device to deliver the pacing pulse to the patient according to an atrio-ventricular synchronous pacing mode:
performing, by the processing module, an intrinsic conduction check;
in response to detecting intrinsic conduction based on the intrinsic conduction check, controlling, by the processing module, the leadless pacing device to return to the sensing without pacing mode; and
in response to not detecting intrinsic conduction based on the intrinsic conduction check, controlling, by the processing module, the leadless pacing device to remain in the atrio-ventricular synchronous pacing mode.

15. A leadless pacing system comprising:
a leadless pacing device configured to sense an electric cardiac signal and configured to operate in a sensing without pacing mode and an atrio-ventricular synchronous pacing mode; and
a processing module configured to:
receive the electrical cardiac signal sensed by a leadless pacing device while the leadless pacing device is in the sensing without pacing mode,
detect, based on the electrical cardiac signal, an atrial activation event,
determine, based on the electrical cardiac signal, a ventricular sense event was not detected within a ventricular event detection window that begins at the atrial activation event, and
control the leadless pacing device to switch from the sensing without pacing mode to the atrio-ventricular synchronous pacing mode based on the determination that the ventricular sense event was not detected within the ventricular event detection window, wherein the processing module is configured to control the leadless pacing device to switch to the atrio-ventricular synchronous pacing mode by at least controlling the leadless pacing device to deliver a pacing pulse to the patient according to the atrio-ventricular synchronous pacing mode after detecting an additional atrial activation event.

16. The leadless pacing system of claim 15, comprising means for sensing of a first cardiac cycle and a second cardiac cycle immediately following the first cardiac cycle wherein the processing module is configured to control the leadless pacing device to deliver the pacing pulse to the patient according to the atrio-ventricular synchronous pacing mode by at least controlling the leadless pacing device to deliver the pacing pulse to the patient according to the atrio-ventricular synchronous pacing mode in the first cardiac cycle, wherein the processing module is further configured to, in the second cardiac cycle, control the leadless pacing device to switch from the atrio-ventricular synchronous pacing mode to the sensing without pacing mode.

17. The leadless pacing system of claim 16, wherein the electrical cardiac signal comprises a first electrical cardiac signal and the atrial activation event comprises a first atrial activation event, wherein the processing module is configured to, after controlling the leadless pacing device to switch from the atrio-ventricular synchronous pacing mode to the sensing without pacing mode: receive a second electrical cardiac signal of the patient sensed by the leadless pacing device after the first cardiac cycle and while the leadless pacing device is in the sensing without pacing mode;
detect, based on the second electrical cardiac signal, a second atrial activation event;
determine, based on the second electrical cardiac signal, the ventricular sense event was not detected within the ventricular event detection window that begins at the second atrial activation event; and
control the leadless pacing device to switch from the sensing without pacing mode to the atrio-ventricular synchronous pacing mode based on the determination that the ventricular sense event was not detected within the ventricular event detection window that begins at the second atrial activation event.

18. The leadless pacing system of claim 15, wherein the processing module is further configured to control the leadless pacing device to switch from the sensing without pacing mode to the atrio-ventricular synchronous pacing mode by at least:
in response to determining the ventricular sense event was not detected within the detection window, incrementing a counter,
after incrementing the counter, determining, by the processing module, whether a value of the counter is greater than or equal to a threshold value, and in response to determining the value of the counter is greater than or equal to a threshold value, controlling, by the processing module, the leadless pacing device to deliver the pacing pulse according to the atrio-ventricular synchronous pacing.

19. The leadless pacing system of claim 18, wherein the threshold value is one.

20. The leadless pacing system of claim 18, wherein the threshold value is two or three.

21. The leadless pacing system of claim 15, wherein the processing module is configured to detect the atrial activation event by at least detecting a P wave in the sensed electrical cardiac signal.

22. The leadless pacing system of claim 15, wherein the processing module is configured to detect the atrial activation event by at least detecting delivery of an atrial pacing pulse by a medical device different than the leadless pacing device.

23. The leadless pacing system of claim 15, further comprising a means for sensing A-A intervals and a memory that stores the A-A intervals for a predetermined number of prior cardiac cycles of the patient, wherein the processing module is further configured to determine the ventricular event detection window based on the stored A-A intervals.

24. The leadless pacing system of claim 23, wherein the processing module is configured to determine the ventricular event detection window by at least determining at least one of: a mean A-A interval of the stored A-A intervals, a median A-A interval of the stored A-A intervals, a greatest A-A interval of the stored A-A intervals, a shortest A-A interval of the stored A-A intervals, or a most recent A-A interval of the stored A-A intervals.

25. The leadless pacing system of claim 24, wherein the processing module is configured to determine the ventricular event detection window by at least determining a predetermined percentage of the at least one of the mean A-A interval, the median A-A interval, the greatest A-A interval, the shortest A-A interval, or the most recent A-A interval.

26. The leadless pacing system of claim 23, wherein the processing module is configured to determine the ventricular event detection window by at least selecting the smaller of a first ventricular event detection window determined based on the stored A-A intervals for a predetermined number of prior cardiac cycles or a second, fixed ventricular event detection window stored by the leadless pacing device.

27. The leadless pacing system of claim 15, wherein the processing module is configured to receive data indicating a duration of the ventricular event detection window from a medical device programmer.

28. The leadless pacing system of claim 15, wherein the processing module is configured to, after controlling the leadless pacing device to deliver the pacing pulse to the patient according to an atrio-ventricular synchronous pacing mode:
    control the leadless pacing device to perform an intrinsic conduction check,
    in response to detecting intrinsic conduction based on the intrinsic conduction check, control the leadless pacing device to return to the sensing without pacing mode, and
    in response to not detecting intrinsic conduction based on the intrinsic conduction check, control the leadless pacing device to remain in the atrio-ventricular synchronous pacing mode.

29. The leadless pacing system of claim 15, wherein the processing module is housed in the leadless pacing device.

* * * * *